US011235023B2

(12) United States Patent
Ludin et al.

(10) Patent No.: US 11,235,023 B2
(45) **Date of Patent: *Feb. 1, 2022**

(54) BETA-HAIRPIN PEPTIDOMIMETIC WITH ELASTASE INHIBITORY ACTIVITY AND AEROSOL DOSAGE FORMS THEREOF

(71) Applicant: POLYPHOR AG, Allschwil (CH)

(72) Inventors: Christian Ludin, Oberwil (CH); Manfred Keller, Munich (DE)

(73) Assignee: POLYPHOR AG, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/305,518

(22) PCT Filed: May 31, 2017

(86) PCT No.: PCT/EP2017/025156

§ 371 (c)(1),
(2) Date: Nov. 29, 2018

(87) PCT Pub. No.: WO2017/207117

PCT Pub. Date: Dec. 7, 2017

(65) Prior Publication Data

US 2020/0230202 A1 Jul. 23, 2020

(30) Foreign Application Priority Data

May 31, 2016 (EP) .................................... 16020210

(51) Int. Cl.

| | |
|---|---|
| ***A61K 38/12*** | (2006.01) |
| ***A61P 11/08*** | (2006.01) |
| ***A61K 9/00*** | (2006.01) |

(52) U.S. Cl.

CPC ............ *A61K 38/12* (2013.01); *A61K 9/0073* (2013.01); *A61P 11/08* (2018.01)

(58) Field of Classification Search

CPC ........ A61K 38/12; A61K 9/0073; A61P 11/08
See application file for complete search history.

(56) References Cited

U.S. PATENT DOCUMENTS

2009/0054345 A1* 2/2009 DeMarco ................ A61P 29/00
514/20.2

FOREIGN PATENT DOCUMENTS

| | | | |
|---|---|---|---|
| EP | 2 567 691 | A1 | 3/2013 |
| WO | WO 98/19694 | A1 | 5/1998 |
| WO | WO 2006/079019 | A2 | 7/2006 |
| WO | WO 2006/087001 | A1 | 8/2006 |
| WO | WO 2007/090646 | A1 | 8/2007 |
| WO | WO 2007/091266 | A2 | 8/2007 |
| WO | WO 2008/025560 | A1 | 3/2008 |
| WO | WO 2015/096672 | A1 | 7/2015 |
| WO | WO 2015/096873 | A1 | 7/2015 |

OTHER PUBLICATIONS

Griese et al., "α-1-Antitrypsin inhalation reduces airway inflammation in cystic fibrosis patients", European Respiratory Journal, vol. 29, No. 2, 2007, pp. 240-250 (11 pages).
Hohenegger, "Novel and Current Treatmeant Concepts Using Pulmonary Drug Delivery", Current Pharmaceutical Design, vol. 16, 2010, pp. 2484-2482 (9 pages).
Knoch et al., "The customised electronic nebuliser: a new category of liquid aerosol drug delivery systems", Expert Opin. Drug Deliv., vol. 2, No. 2, 2005, pp. 377-390 (14 pages).
Koga et al., "Inhibition of neutrophil elastase attenuates airway hyperresponsiveness and inflammation in a mouse model of secondary allergen challenge: neutrophil elastase inhibition attenuates allergie airway responses", Respiratory Research, vol. 14, No. 8, 2013, pp. 1-13.
Korkmaz et al., "Neutrophil elastase, proteinase 3 and cathepsin G: Physiochemical properties, activity and physiopathological functions", Biochemie, vol. 90, 2008 (available online Oct. 25, 2007), pp. 227-242 (16 pages).
Ohbayashi, "Neutrophil elastase inhibitors as treatment for COPD". Expert Opin. Investig. Drugs. vol. 11, No. 7, 2002, pp. 965-980 (16 pages).
Owen et al., "The cell biology of leukocyte-mediated proteolysis", Journal of Leukocyte Biology, vol. 65, Feb. 1999, pp. 137-150 (14 pages).
Patton et al., "Inhaling medicines: delivering drugs to the body through the lungs", Nature Reviews, vol. 6, Jan. 2007, pp. 67-74 (8 pages).
Siekmeier, "Lung Deposition of Inhaled Alpha-1-Proteinase Inhibitor (Alpha1-PI)—Problems and Experience of Alpha 1-PI Inhalation Therapy In Patients With Hereditary Alpha1-PI Deficiency and Cystic Fibrosis", Eur J Med Res., vol. 15, Nov. 4, 2010, pp. 164-174 (11 pages).
Van der Geld et al., "Proteinase 3, Wegener's autoantigen: from gene to antigen", Journal of Leukocyte Biology, vol. 69, Feb. 2001, pp. 177-190 (14 pages).

(Continued)

*Primary Examiner* — Sudhakar Katakam
(74) *Attorney, Agent, or Firm* — Birch, Stewart, Kolasch & Birch, LLP

(57) ABSTRACT

The present invention relates to pharmaceutical aerosols comprising a β-hairpin peptidomimetic of formula cyclo(-OctG-Glu-Thr-Ala-Ser-Ile-Pro-Pro-Gln-Lys-Tyr-$^D$Pro-Pro-), or a pharmaceutically acceptable salt thereof, having inhibitory activity against human neutrophil elastase. It further relates to solid or liquid pharmaceutical compositions and kits for preparing and administering such aerosols. The invention can be used for the prevention, management or treatment of pulmonary diseases, such as alpha-1 antitrypsin deficiency (AATD), cystic fibrosis (CF), non-cystic fibrosis bronchiactasis (NCFB), or chronic obstructive pulmonary disease (COPD), or infections, or diseases, or conditions of the lungs, being mediated by or resulting from human neutrophil elastase activity. Thus, the invention further relates to a pharmaceutical composition or a pharmaceutical aerosol comprising the active compound cyclo(-OctG-Glu-Thr-Ala-Ser-Ile-Pro-Pro-Gln-Lys-Tyr-$^D$Pro-Pro-), or any pharmaceutically acceptable salt thereof, for use in a method for the prevention, management or treatment of diseases or conditions of the lungs being mediated by or resulting from human neutrophil elastase activity in a subject.

14 Claims, 3 Drawing Sheets

(56) References Cited

OTHER PUBLICATIONS

International Search Report (PCT/ISA/210) issued in PCT/EP2017/025156, dated Aug. 16, 2017.

Written Opinion (PCT/ISA/237) issued in PCT/EP2017/025156, dated Aug. 16, 2017.

* cited by examiner

BETA-HAIRPIN PEPTIDOMIMETIC WITH ELASTASE INHIBITORY ACTIVITY AND AEROSOL DOSAGE FORMS THEREOF

FIELD OF THE INVENTION

The invention relates to pharmaceutical aerosols comprising a β-hairpin peptidomimetic of formula cyclo(-OctG-Glu-Thr-Ala-Ser-Ile-Pro-Pro-Gln-Lys-Tyr-$^{D}$Pro-Pro-), or a pharmaceutically acceptable salt thereof, being specifically disclosed in WO2006/087001 A1 and having inhibitory activity against human neutrophil elastase. It further relates to solid or liquid pharmaceutical compositions and kits for preparing and administering such aerosols. The invention can be used for the prevention, management or treatment of diseases or conditions of the lungs being mediated by or resulting from human neutrophil elastase activity, e.g. pulmonary diseases, such as alpha-1 antitrypsin deficiency (AATD), cystic fibrosis (CF), non-cystic fibrosis bronchiactasis (NCFB), or chronic obstructive pulmonary disease (COPD), or infections of the lungs causing diseases or conditions of the lungs, being mediated by human neutrophil elastase activity. Thus, the invention further relates to a pharmaceutical composition or a pharmaceutical aerosol comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, for use in a method for the prevention, management or treatment of diseases or conditions of the lungs being mediated by or resulting from human neutrophil elastase activity in a subject.

BACKGROUND OF THE INVENTION

Human neutrophil elastase (human NE), a member of the serine protease family, constitutes an important therapeutic target. Besides cathepsin G and proteinase 3 it is intimately involved in the modulation of activities of cytokines and their receptors. Particularly at sites of inflammation, high concentration of human NE is released from infiltrating polymorphonuclear cells in close temporal correlation to elevated levels of inflammatory cytokines, strongly indicating that this protease is involved in the control of cytokine bioactivity and availability (U. Bank, S. Ansorge, *J. Leukoc. Biol.* 2001, 69, 177-90). Human NE is known to be mainly responsible for extracellular proteolysis and contributes to tissue damage by catalyzing the hydrolysis of a wide variety of matrix macromolecules, plasma proteins, inflammatory mediators, and cell surface receptors with important local and systemic consequences (C. A. Oven; E. J. Campbell; *J. Leukoc. Biol.* 1999, 65, 137-150). Thus, inhibitors of human NE are valuable novel drug candidates for infectious inflammatory diseases, including lung diseases like chronic obstructive pulmonary disease (COPD), acute respiratory distress syndrome (ARDS), cystic fibrosis (CF) and ischemic-reperfusion injury, (H. Ohbayashi, *Expert Opin. Investig. Drugs* 2002, 11, 965-980; B. Korkmaz, T. Moreau, F. Gauthier, *Biochimie* 2008, 90, 227). They can meet a significant need for new therapies effectively preventing or treating and/or mitigating these diseases or conditions.

Routes of administration can be classified whether the effect of the drug is local (topical administration) or systemic (enteral or parenteral administration). The delivery of pharmaceuticals to the bronchi and lungs (pulmonary drug delivery) has been used for the local treatment of diseases and conditions of the respiratory system. However, the feasibility of inhalation as an alternate route of administration for treatment of systemic diseases utilising the large surface of the lungs for absorption has been demonstrated as well (J. S. Patton, P. R. Byron, *Nat. Rev. Drug Discov.* 2007, 6, 67-74; M. Hohenegger, *Curr. Pharm. Des.* 2010, 16, 2484-2492).

In particular, drug substances can be delivered to the respiratory system as aerosolized dry powders or aerosolized liquids, the latter being either solutions or dispersions, such as drug substance suspensions. Various devices have been developed to convert a solid or liquid composition into an aerosol to enable inhalation. For the conversion of aqueous-based drug substance solutions or suspensions into inhalable aerosols nebulizers are normally used. They are particularly useful for diseases that require high pulmonary doses, e.g. CF, and patients, e.g. children, who are unable to coordinate or achieve flow rates necessary for use of other inhalation devices (M. Knoch, M. Keller, *Expert Opin. Drug Del.* 2005, 2, 377-390).

Inhalation of drug substances may be favourable for the prophylaxis and/or treatment of respiratory tract infections and/or diseases associated with neutrophil elastase activity. There is evidence that airway infiltration by neutrophils will lead to an increase in neutrophil elastase within the extracellular compartment and thereby inducing deleterious effects. In a mouse model of neutropil allergen challenge it could be demonstrated that the inhibition of neutrophil elastase by sivelelstat attenuates airway hyperresponsiveness and inflammation (H. Koga, N. Miyahara et al., *Respir. Res.* 2013, 14:8). In a different mouse model delivery of unglycosylated rhalpha1PI, a recombinant form of the elastase inhibitor alpha-1-proteinase inhibitor (alpha1PI), to the airway surface of CD-1 mice by nasal instillation was found to be highly protective against elastase-mediated injury, even significantly more protective than glycosylated blood-derived alpha1PI. These results suggest that aerosol delivery of rhalpha1PI could be an effective strategy for controlling elastase-dependent pathophysiology associated with cystic fibrosis lung disease. Recently, R. Siekmeier summarized the results of so far completed clinical studies aiming at lung deposition of inhaled alpha1PI of patients with hereditary alpha1PI-deficiency or cystic fibrosis (*Eur. J. Med. Res.* 2010, 15 [Suppl. II], 164). For both therapeutic areas most of the studies indicate that the administration of alpha1PI by inhalation may serve as a potent therapy to neutralize the excess of inflammatory proteins and neutrophil elastase. Whereas the latter effects do not automatically lead to improvements on patient's lung function, a clear reduction of airway inflammation after alpha1PI treatment may precede pulmonary structural changes (M. Griese, P. Latzin et al., *Eur. Respir. J.* 2007, 29, 240).

Generally, the benefit of drug substance delivery via inhalation is that it can afford delivery of sufficient therapeutic dosages of the drug directly to the primary site of action, e.g. in case of respiratory diseases, while minimizing the risks of systemic toxicity. Additionally, suboptimal pharmacokinetics and/or pharmacodynamics associated with systemic drug exposure may be avoided. Furthermore, inhalation (at home) is a more convenient mode of administration than intravenous injection (medical ward).

Still, the effectiveness of a therapy based on inhaled drug substance delivery depends mainly on the drug which is selected, a pharmaceutical composition thereof suitable for inhalation and the device that is employed. Thus, there is a strong need for further pharmaceutical compositions, aerosols and therapeutic kits which are suitable for the prevention, management or treatment of diseases or conditions being mediated by or resulting from human neutrophil elastase activity improving the outcome of presently known therapies and/or overcoming the disadvantages of presently known therapies.

SUMMARY OF THE INVENTION

The invention provides a pharmaceutical aerosol for pulmonary administration comprising a dispersed liquid phase and a continuous gas phase. The dispersed liquid phase comprises aqueous droplets comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof. The droplets of the dispersed phase have a mass median diameter from about 1.5 μm to about 5 μm with a droplet size distribution having a geometrical standard deviation from about 1.2 to about 1.7. Further provided by the invention is the pharmaceutical aerosol for pulmonary administration comprising a dispersed liquid phase and a continuous gas phase, wherein the dispersed liquid phase comprises aqueous droplets comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, for use in a method for the prevention, management or treatment of diseases or conditions of the lungs being mediated by or resulting from human neutrophil elastase activity in a subject.

In another aspect, the invention provides liquid and solid pharmaceutical compositions from which the above aerosol can be prepared. The liquid composition comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in a concentration within a range from about 4 mg/mL to about 100 mg/mL, preferably, within a range from about 17 mg/mL to about 95 mg/mL, or about 35 mg/mL to about 95 mg/mL, respectively, and more preferably, within a range from about 70 mg/mL to about 95 mg/mL.

In still another aspect, the invention provides a kit comprising a nebulizer and a liquid or solid composition, wherein the nebulizer is adapted to aerosolize the liquid composition into an aerosol, as described above. Further provided by the invention is a kit comprising a nebulizer and a liquid or solid composition, wherein the nebulizer is adapted to aerosolize the liquid composition into an aerosol, as described above, for use in a method for the prevention, management or treatment of diseases or conditions of the lungs being mediated by or resulting from human neutrophil elastase activity in a subject.

In still another aspect, the invention further discloses a method of preparing and delivering an aerosol for pulmonary administration. The method comprises the step of providing a liquid pharmaceutical composition comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in a concentration within a range from about 4 mg/mL to about 100 mg/mL, preferably, within a range from about 17 mg/mL to about 95 mg/mL, or about 35 mg/mL to about 95 mg/mL, respectively, and more preferably, within a range from about 70 mg/mL to about 95 mg/mL, or providing a solid pharmaceutical composition for preparing the liquid composition, wherein the composition comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and wherein the solid composition is dissolvable or dispersible in an aqueous liquid solvent, and wherein the liquid composition comprises a concentration within a range from about 4 mg/mL to about 100 mg/mL, preferably, within a range from about 17 mg/mL to about 95 mg/mL, or about 35 mg/mL to about 95 mg/mL, respectively, and more preferably, within a range from about 70 mg/mL to about 95 mg/mL, of the active compound, or any pharmaceutically acceptable salt thereof, and the step of providing a nebulizer capable of aerosolizing said liquid pharmaceutical composition at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, per minute, the nebulizer being further adapted to emit an aerosol comprising a dispersed liquid phase having a mass median diameter from about 1.5 μm to about 5 μm, and having a droplet size distribution having a geometrical standard deviation from about 1.2 to about 1.7. In a subsequent step the nebulizer is operated to aerosolize the liquid pharmaceutical composition which finally can be inhaled by mammals, more preferably, by human subjects.

In still another aspect, the invention provides a pharmaceutical composition comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and optionally one or more pharmaceutically acceptable diluents, excipients or carriers, for use in a method for the prevention, management or treatment of diseases or conditions of the lungs being mediated by or resulting from human neutrophil elastase activity in a subject.

In still another aspect, the invention provides a kit comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and a package insert wherein the package insert comprises instructions for treating a subject for diseases or conditions of the lungs being mediated by or resulting from human neutrophil elastase activity using the active compound.

Figure 1:
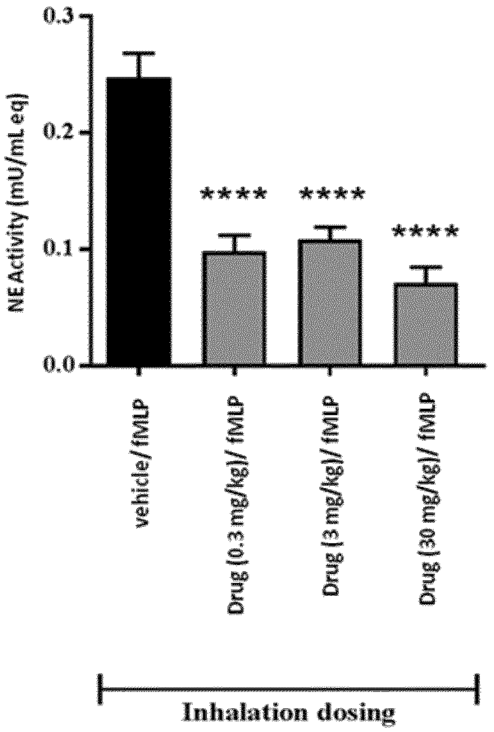
FIGS. 1 and 2 show the effects of cyclo(-OctG-Glu-Thr-Ala-Ser-Ile-Pro-Pro-Gln-Lys-Tyr-$^{D}$Pro-Pro-) administered by inhalation in a LPS/fMLP model of neutrophil activation in the rat. BAL supernatants from the tracheae of dead rats were analyzed for neutrophil elastase activity. Data are displayed versus the vehicle control. Data are depicted both as means (FIG. 1) and as individual data points together with their corresponding mean and s.e.m. values (FIG. 2).

Strong inhibition (>90%) of active elastase in sputum over several hours after single dose administration of active compound in all dose groups can be derived.

DETAILED DESCRIPTION OF THE INVENTION

In a first aspect, the invention provides a pharmaceutical aerosol for pulmonary administration comprising a dispersed liquid phase and a continuous gas phase. The dispersed liquid phase comprises aqueous droplets comprising the active compound cyclo(-OctG-Glu-Thr-Ala-Ser-Ile-Pro-Pro-Gln-Lys-Tyr-$^D$Pro-Pro-), or any pharmaceutically acceptable salt thereof. The droplets of the dispersed phase have a mass median diameter from about 1.5 μm to about 5 μm with a droplet size distribution having a geometrical standard deviation from about 1.2 to about 1.7.

The aerosol of the invention is for pulmonary delivery, which is preferable achieved via oral inhalation of the aerosol. As used herein in the description and the claims, pulmonary delivery means aerosol delivery to any part or feature of the lungs including the so-called deep lungs, the peripheral lungs, the alveoli, the bronchi and the bronchioli.

Conditions of the pulmonary target regions in which the prevention, management or treatment of mammals, more preferably, of human subjects, using the aerosol of the invention is potentially useful include diseases or conditions of the lungs being mediated by or resulting from human neutrophil elastase activity, e.g. in particular, pulmonary diseases, such as alpha-1 antitrypsin deficiency (AATD), cystic fibrosis (CF), non-cystic fibrisis bronchiactasis (NCFB), or chronic obstructive pulmonary disease (COPD), or infections of the lungs causing diseases or conditions of the lungs, being mediated by human neutrophil elastase activity.

As used herein in the description and the claims, an aerosol is a dispersion of a solid and/or liquid phase in a gas phase. The dispersed phase, also termed discontinuous phase, comprises multiple solid and/or liquid particles. Both basic physical types of aerosols, i.e. solid and liquid dispersions in a gas phase, may be used as pharmaceutical aerosols.

According to the present invention, the aerosol comprises a dispersed liquid phase and a continuous gas phase. Such aerosols are sometimes referred to as "liquid aerosols" or aerosolized liquids. It should be noted that the requirement of a dispersed liquid phase does not exclude the presence of a solid phase. In particular, the dispersed liquid phase may itself represent a dispersion, such as a suspension of solid particles in a liquid.

The continuous gas phase is to be selected from any gas or mixture of gases which is pharmaceutically acceptable. For example, air or compressed air as gas phase is most common in inhalation therapy using nebulizers as aerosol generators. Alternatively, other gases and gas mixtures, such as air enriched with oxygen, or mixtures of nitrogen and oxygen may be used. The use of air as continuous gas phase is most preferred.

The active compound is cyclo(-OctG-Glu-Thr-Ala-Ser-Ile-Pro-Pro-Gln-Lys-Tyr-$^D$Pro-Pro-), or any pharmaceutically acceptable salt thereof, having inhibitory activity against human neutrophil elastase. Structurally, the active compound is a homodetic, cyclic tridecapeptide, wherein OctG is (S)-2-aminodecanoic acid and $^D$Pro is D-proline. The abbreviations (3-letter code) for the remaining amino acid residues are as generally recognized. All amino acid residues are in L-configuration except one D-proline residue.

As used herein in the description and the claims the active compound cyclo(-OctG-Glu-Thr-Ala-Ser-Ile-Pro-Pro-Gln-Lys-Tyr-$^D$Pro-Pro-) should be understood as to include the respective solvates.

Solvates as well as salts are categories of forms in which the active compound cyclo(-OctG-Glu-Thr-Ala-Ser-Ile-Pro-Pro-Gln-Lys-Tyr-$^D$Pro-Pro-) may be used as an active ingredient in a pharmaceutical composition.

Salts are neutral compounds composed of ions, i.e. cations and anions. If the active compound can act like an acid, potentially useful salts may be formed with inorganic cations, such as sodium, potassium, calcium, magnesium and/or ammonium, or with organic cations, such as those derived from arginine, lysine, glycine, and/or ethylenediamine. If the active compound (or parts thereof) can act like a base, as for example the residue of Lys being one of the amino acid residues of cyclo(-OctG-Glu-Thr-Ala-Ser-Ile-Pro-Pro-Gln-Lys-Tyr-$^D$Pro-Pro-), then potentially useful salts may be formed with inorganic anions, such as chloride, bromide, iodide, phosphate (mono- or dibasic), sulfate, nitrate, acetate, trifluoroacetate, propionate, butyrate, maleate, fumarate, methanesulfonate, ethanesulfonate, 2-hydroxyethylsulfonate, n-propylsulfonate, isopropylsulfonate, lactate, malate, and/or citrate.

The term pharmaceutically acceptable salt or pharmaceutical salt is used to refer to an ionisable drug or active compound that has been combined with a counter ion to form a neutral complex. Converting a drug or active compound into a salt through this process can, for example, increase its chemical stability, render the complex easier to administer and/or allow manipulation of the agent's pharmacokinetic profile.

In a preferred embodiment of the invention, the counter ion of the active compound is acetate.

The aerosol is further characterized in that the droplets of the dispersed liquid phase have a mass median diameter from about 1.5 μm to about 5 μm with a droplet size distribution having a geometrical standard deviation from about 1.2 to about 1.7. The mass median diameter (MMD), as used herein in the description and the claims, is the mass median diameter of the dispersed liquid phase as measured by laser diffraction. Various appropriate analytical apparatuses to determine the MMD are known and commercially available, such as the Malvern MasterSizer X or Malvern SprayTec. The geometric distribution including the geometric standard deviation (GSD) of the aerosolized liquid particles or droplets may be determined simultaneously with the MMD. The GSD describes how spread out is a set of numbers the preferred average of which is the geometric mean.

In a preferred embodiment, the aerosol is for pulmonary delivery and the dispersed liquid phase of such an aerosol has a MMD in the range from about 2.0 μm to about 4.5 μm and a GSD in the range from about 1.2 to about 1.7. More preferably, the aerosol of the invention has a MMD in the range from about 2.5 μm to about 3.5 μm and a GSD in the range from about 1.4 to about 1.6. Each of these sets of combinations is particularly useful to achieve a high local concentration of the active compound in the lungs, including the bronchi and bronchioli, relative to the amount of active compound which is aerosolized.

In another preferred embodiment, the aerosol is emitted from an aerosol generator at a rate of at least about 0.1 mL/min. In another embodiment, the (total) output rate being the rate at which the aerosol is emitted from the aerosol generator is at least about 0.150 mL/min or at least about 150 mg/min for those liquid aerosols the densities of which are—for practical purposes—close to 1 g/mL, i.e. within the range from about 0.95 g/mL to about 1.05 g/mL. In further embodiments, the output rate is within the range from about 200 mg/min to about 700 mg/min, or from about 250 mg/min to about 650 mg/min, respectively.

In another preferred embodiment, the aerosol is emitted from an aerosol generator at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, per minute. The (mean) delivery rate of a drug or active compound is one of two discrete metrics or parameters being defined and measured according to e.g. Ph. Eur. (Pharmacopeia Europaea) 2.9.44 and/or USP (United States Pharmacopeia) 1601 to determine the amount of drug or active compound a patient might be expected to receive during a treatment period. In further embodiments, the mean delivery rate of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, is within the range from about 3 mg to about 25 mg per minute or within the range from about 5 mg to about 18 mg per minute, respectively.

Appropriate aerosol generators, in particular nebulizers, which are suitable for generating the aerosol(s) described herein in the description and the claims are discussed in more detail herein-below.

In another aspect, the present invention is directed to a liquid pharmaceutical composition for preparing the aerosol as described above comprising the active compound cyclo (-OctG-Glu-Thr-Ala-Ser-Ile-Pro-Pro-Gln-Lys-Tyr-$^{D}$Pro-Pro-), or any pharmaceutically acceptable salt thereof, in a concentration within a range from about 4 mg/mL to about 100 mg/mL.

As defined herein in the description and the claims, a liquid pharmaceutical composition is a liquid material which comprises at least one active compound and at least one pharmaceutically acceptable, pharmacologically substantially inert excipient. It should be noted that the term "liquid composition" does not necessarily mean that no solid material is present. For example, a liquid suspension representing a dispersion of solid particles in a continuous liquid phase is also embraced in the above term.

Preferably, the liquid composition from which the aerosol is prepared is an aqueous composition; consequently, water is the predominant liquid constituent of such composition. Solvents and co-solvents other than water should be avoided. In another embodiment, the composition comprises at least about 80 wt.-% of water. In yet another embodiment, at least about 90 wt.-% of the liquid constituents of the composition is water.

If the incorporation of a non-aqueous solvent, such as ethanol, glycerol, propylene glycol or polyethylene glycol, cannot be avoided, the excipient should be selected carefully and in consideration of its physiological acceptability and the therapeutic use of the composition. According to a preferred embodiment, the composition is substantially free of non-aqueous solvents.

The concentration of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in the liquid composition is within a range from about 4 mg/mL to about 100 mg/mL. Preferably, the concentration of the above active compound, or any pharmaceutically acceptable salt thereof, is within the range from about 17 mg/mL to about 95 mg/mL, or about 35 mg/mL to about 95 mg/mL, respectively, or, more preferred, about 70 mg/mL to about 95 mg/mL. A high concentration of an active compound in a composition suitable to be aerosolized provides for patient convenience and compliance: The higher such concentration the smaller the total volume of liquid composition comprising the effective dose of the active compound to be inhaled and the shorter the total time being necessary for inhalation of such an effective dose.

The dynamic viscosity of the liquid composition has an influence on the efficiency of nebulization and on the particle size distribution of the aerosol formed by nebulization. The dynamic viscosity should preferably be adjusted to a range from about 0.8 mPas to about 1.7 mPas. In other embodiments, the dynamic viscosity is in the range from about 1.0 mPas to about 1.7 mPas, or in the range from about 1.2 mPas to about 1.6 mPas, respectively.

In order to obtain an aerosol which is highly suitable for pulmonary administration, the surface tension of the liquid composition of the invention should preferably be adjusted to a range from about 25 mN/m to about 80 mN/m, more preferably, to a range from about 30 mN/m to about 70 mN/m, or even more preferably, to a range from about 45 mN/m to about 55 mN/m.

In general, the quality of an aerosol and the efficiency of the nebulisation could be adversely affected in the lower parts of the above presented embodiments; however, the results of the studies described below indicate that there are no significant changes in the performances of the liquid compositions of the invention in the above respect.

It is well known in the art that addition of a surfactant to an aqueous liquid composition may result in a surface tension being reduced fairly markedly below that of water or physiological buffer solution. Therefore, a compromise has to be found in each case depending on the intended application.

In order to be well-tolerated an aerosol should—as far as possible—have a physiological tonicity or osmolality. Thus, it may be desirable to incorporate an osmotically active excipient to control the osmolality of the aerosol. Such an excipient, or excipients, if e.g. a combination of substances is used, should be selected to ideally reach an osmolality of the aerosol which does not deviate too much from that of physiological fluids, i.e. from about 150 mOsmol/kg. However, a compromise has again to be found between the physical-chemical and/or pharmaceutical needs on one hand and the physiological requirements on the other hand. In general, an osmolality up to about 800 mOsmol/kg may be acceptable. In particular, an osmolality in the range from about 200 mOsmol/kg to about 600 mOsmol/kg is preferred. In further embodiments, the osmolality is in the range from about 250 mOsmol/kg to about 500 mOsmol/kg or in the range from about 300 mOsmol/kg to about 450 mOsmol/kg, respectively.

One approach to improve the effectiveness and/or efficacy of the composition may be to enhance the local retention time of the composition after deposition of the aerosol in the target regions. For example, a prolonged residence time of the deposited composition in the lungs may lead to a higher continuous exposure of the active compound at the site of action. At the same time, it may reduce the required frequency of administration and therefore, enhance patient convenience and compliance.

In order to achieve a prolonged retention of the active compound in general, various formulation strategies may be pursued, e.g. conversion of the highly water soluble active compound into a less soluble solid form, such as a poorly soluble salt. As a consequence, the compound is present in the aerosol in undissolved form, such as in form of a micro- or nanosuspension. Upon deposition of the aerosol droplets, the liquid phase of the composition combines with the physiological fluid, e.g. mucus, and allows the drug to dissolve.

A different formulation strategy is based on the fact that polymeric excipient(s), as described below, may have an effect on the release of the active compound from the formulation, and/or on the local residence time of the composition after deposition onto the target tissue. Therefore, such excipients affect the local bioavailability of the active compound at the site of action as well.

In one of the preferred embodiments, the active compound cyclo(-OctG-Glu-Thr-Ala-Ser-Ile-Pro-Pro-Gln-Lys-Tyr-$^{D}$Pro-Pro-), or any pharmaceutically acceptable salt thereof, is formulate with a polymeric excipient to effect slow release and prolonged local retention. Potentially suitable polymers include, in particular, pharmaceutically acceptable water-soluble or water-dispersible polymers, such as methylcellulose, hydroxyethylcellulose, alginate, galactomannan, dextran, agar, guar gum, tragacanth, and mixtures thereof.

If one or several polymeric excipients are present in the liquid composition of the invention, care should be taken of the influence on the dynamic viscosity of such a composition in order to ensure efficient aerosolization. Thus, the dynamic viscosity should not exceed about 1.7 mPas. In general, the exact grade of the polymer(s) and the presence of other excipients should be considered to determine the content of the polymer(s) in such liquid composition.

It is known that other excipients, namely complexing agents, such as cyclodextrins, di- or multivalent metal salts, such as calcium-magnesium- or aluminium salts, chelating agents, such as ethylenediaminetetraacetic acid including its salts, or amphiphilic agents, such as phospholipids or lecithins, may in a similar manner prolong the release of the active compound as e.g. polymeric excipients.

The liquid composition of the invention may comprise further pharmaceutically acceptable excipients, e.g. osmotic agents, such as inorganic salts; excipients for adjusting and/or buffering the pH, such as organic or inorganic salts, acids and bases, bulking agents and lyophilisation aids, such as sucrose and lactose, sugar alcohols, like mannitol, sorbitol, and xylitol, stabilizers and antioxidants, such as vitamin E including its derivatives, lycopene including its derivatives and ascorbic acid, ionic and non-ionic surfactants, such as phospholipids and polysorbates, taste-modifying agents, disintegrants, colouring agents, sweeteners, and/or flavours.

In one of the preferred embodiments, one or more osmotic agents, such as sodium chloride, are incorporated in the composition to adjust the osmolality to a value in a preferred range as outlined herein above. In a more preferred embodiment, the osmotic agent is sodium chloride.

In order to provide a well tolerated aerosol, the preparation according to the invention should be adjusted to a euhydric pH. The term “euhydric” implies that there may be a difference between pharmaceutical and physiological requirements so that a compromise has to be found which, for example, ensures that, on one hand, the preparation is sufficiently stable during storage, but, on the other hand, is still well tolerated. Preferably, the pH value lies in the slightly acidic to neutral region, i.e. between about 4 and about 8. In general, deviations towards a weakly acidic milieu are tolerated better than an alkaline shift. Particularly preferred is a composition having a pH lying within the range from about 4.5 and about 7.5.

For adjusting the pH of the composition of the invention and/or buffering such composition, physiologically acceptable acids, bases, salts, and combination of these may be used. Suitable excipients for lowering the pH value and/or as acidic components of a buffer system are strong mineral acids, such as sulphuric acid and hydrochloric acid. Inorganic and organic acids of medium strength, such as phosphoric acid, citric acid, tartaric acid, succinic acid, fumaric acid, methionine, lactic acid, acetic acid, glucuronic acid, as well as acidic salts, such as hydrogen phosphates with sodium or potassium, may be used as well. Suitable excipients for raising the pH value and/or as basic components of a buffer system are mineral bases, such as sodium hydroxide, or other alkali and alkaline earth hydroxides and oxides, such as magnesium hydroxide, calcium hydroxide, or basic ammonium salts, such as ammonium hydroxide, ammonium acetate, or basic amino acids, such as lysine, or carbonates, such as sodium or magnesium carbonate, sodium hydrogen carbonate, or citrates, such as sodium citrate.

In a preferred embodiment, the composition of the invention comprises at least one excipient to adjust the pH. In a more preferred embodiment, that excipient is sodium hydroxide.

Mainly for pharmaceutical reasons the chemical stabilisation of the composition of the invention by further additives may be indicated. The most common degradation reactions of a chemically defined active compound in aqueous preparations comprise, in particular, hydrolysis reactions which may be limited primarily by optimal pH adjustment, as well as oxidation reactions. As the active compound cyclo(-OctG-Glu-Thr-Ala-Ser-Ile-Pro-Pro-Gln-Lys-Tyr-$^{D}$Pro-Pro-) comprises a lysine residue having a primary amino group, the latter, for example, may be subject to oxidative attack. Therefore, the addition of an antioxidant, or an antioxidant in combination with a synergist, may be advisable or necessary.

Antioxidants are natural or synthetic substances which are capable of preventing or inhibiting the oxidation of the active compound. Antioxidants are primarily ajuvants which are oxidizable and/or act as reducing agents, such as tocopherol acetate, lycopene, reduced glutathione, catalase, peroxide dismutase. Further suitable antioxidants are, for example, ascorbic acid, sodium ascorbate and other salts and derivatives of ascorbic acid, e.g. ascorbyl palmitate, fumaric acid and its salts, malic acid and its salts.

Synergistic substances are those which do not directly act as reactants in oxidation processes, but which counteract such processes by indirect mechanisms, for example, by complexation of metal ions which are known to act catalytically in oxidation processes. Ethylenediaminetetraacetic acid (EDTA) and salts and derivatives thereof, citric acid and salts thereof, malic acid and salts thereof, are such synergistic substances which may act as chelating agents.

In one of the embodiments, the composition of the invention comprises at least one antioxidant. In a further embodiment, the composition comprises both an antioxidant and a chelating agent.

As mentioned above, the composition of the invention may comprise an excipient affecting the taste. A bad taste is extremely unpleasant and irritating, especially in inhalation administration, and can result in non-compliance, and thus, therapy failure. The bad taste is perceived by the patient through that part of the aerosol which precipitates in the oral and pharyngeal region during inhalation. Even if the particle size of the aerosol can be optimized in such a manner that only a small fraction of the preparation precipitates in the above mentioned regions (said fraction being lost for therapy, unless the oral, pharyngeal or nasal mucosa is the target tissue) it is presently hardly possible to reduce said fraction to such an extent that the bad taste of an active compound is no longer perceived. Therefore, the improvement of the taste of a composition or the masking of the taste of an active compound may be crucial.

In order to improve the taste of the composition, one or more potentially useful excipients from the group of sugars, sugar alcohols, salts, flavours, complexing agents, polymers, sweeteners, such as sodium saccharin, aspartame, surfactants may be incorporated.

In a preferred embodiment, the composition of the invention comprises at least one taste-modifying excipient. In a more preferred embodiment, said taste-modifying excipient is sodium saccharin.

In another embodiment, the composition comprises a further active compound, the combination of which with the active compound cyclo(-OctG-Glu-Thr-Ala-Ser-Ile-Pro-Pro-Gln-Lys-Tyr-$^{D}$Pro-Pro-) having a combined or, ideally, a synergistic therapeutic effect.

In case a liquid formulation for aerosolization may not have a sufficiently long shelf life to serve as a suitable formulation for market it may be beneficial to provide a solid composition instead. Such solid composition generally has the potential for a longer shelf life compared to a liquid composition.

The solid composition of the invention comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and at least one excipient. In general, the same excipients as already described above may be selected. Depending on the manufacturing process/method of the solid composition one or more additional excipients may be useful. If the solid composition is, for example, prepared by freeze drying (lyophilization) being one of the preferred methods of preparing such a solid composition, it may be advantageous to incorporate at least one bulking agent and/or lyophilization aid, e.g. a sugar, such as sucrose, fructose, glucose, trehalose, or a sugar alcohol, such as mannitol, sorbitol, xylitol, isomalt.

The solid composition is further characterized in that it is dissolvable or dispersible in an aqueous liquid solvent. As defined herein in the description and the claims, the term “dissolvable” means that the solid composition and the aqueous liquid solvent can be combined to form a solution or colloidal solution, whereas the term “dispersible” should be interpreted to include the formation of liquid dispersions, in particular, emulsions and microsuspensions. The term “aqueous” means that the major liquid constituent of the solvent is water. Solvents and co-solvents other than water should be avoided. In another embodiment, the aqueous liquid solvent comprises at least about 80 wt.-% of water. In yet another embodiment, at least about 90 wt.-% of the liquid constituents of the solvent is water. If the incorporation of a non-aqueous solvent, such as ethanol, glycerol, propylene glycol or polyethylene glycol, cannot be avoided, the excipient should be selected carefully and in consideration of its physiological acceptability and the therapeutic use of the composition. According to a preferred embodiment, the composition is substantially free of non-aqueous solvents. If the incorporation of a non-aqueous solvent, such as ethanol, glycerol, propylene glycol or polyethylene glycol, cannot be avoided, the same precautions have to be considered as described above. According to another preferred embodiment, the aqueous solvent to dissolve or disperse the solid composition is substantially free of non-aqueous solvents.

The amount of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in the solid composition has to correspond to a concentration within a range from about 4 mg/mL to about 100 mg/mL following dissolution or dispersion in an aqueous liquid solvent. More preferably, the amount of the above active compound, or any pharmaceutically acceptable salt thereof, has to correspond to a concentration within the range from about 17 mg/mL to about 95 mg/mL, or about 35 mg/mL to about 95 mg/mL, respectively, or, even more preferred, about 70 mg/mL to about 95 mg/mL, following dissolution or dispersion in an aqueous liquid solvent.

In a further embodiment, the counter ion of the active compound cyclo(-OctG-Glu-Thr-Ala-Ser-Ile-Pro-Pro-Gln-Lys-Tyr-$^{D}$Pro-Pro-) in the solid composition is acetate.

The solid composition of the invention for reconstitution may be part of a pharmaceutical kit. Such kit preferably comprises the solid composition in sterile form. As used herein in the description and the claims the terms “sterile” or “sterility” are defined according to the usual pharmaceutical meaning and thus to be understood as the absence of germs which are capable of reproduction. Sterility is determined with suitable tests which are defined in the relevant pharmacopoeias. According to current scientific standards, a sterility assurance level (SAL) of $10^{-6}$, i.e. assurance of less than one chance in one million that viable micro-organisms are present in a sterilized article), is regarded as acceptable for sterile preparations. In practice, contamination rates may be higher, and contamination rates for aseptically manufactured preparations might amount to about $10^{-3}$. For practical reasons, it remains difficult to demand sterility in an absolute sense. Therefore, the sterility of the composition of the invention should be understood herein in the description and the claims in such manner that said composition meets the requirements of the relevant pharmacopeia with respect to sterility.

The solid composition of the invention may be prepared by providing a liquid composition being similar to the liquid composition ready for aerosolization and subsequently drying it, e.g. by lyophilisation. Similar means that the liquid composition from which the solid composition is prepared by drying may not comprise all solid ingredients of the ready-to-go liquid composition, for example, in the case that the liquid carrier for reconstitution is designed to comprise one or more of the excipients. It is even not necessary, that the concentrations of the ingredients of these two liquid compositions are identical. The solid composition of the invention may even be prepared, for example, by providing the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and, optionally, at least one excipient, in powder form and subsequently mixing such powder with a powder comprising the remaining excipients to finally form a powder mixture.

In another aspect, the invention provides a pharmaceutical kit for the preparation and delivery of a pharmaceutical aerosol for pulmonary administration comprising a dispersed liquid phase and a continuous gas phase, wherein the dispersed liquid phase comprises aqueous droplets comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, has a mass median diameter from about 1.5 μm to about 5 μm, and has a droplet size distribution having a geometrical standard deviation from about 1.2 to about 1.7. The kit is further characterized by comprising an aerosol nebulizer and an composition comprising a concentration within a range from about 4 mg/mL to about 100 mg/mL of the active compound, or any pharmaceutically acceptable salt thereof; or comprising a nebulizer and a solid pharmaceutical composition for preparing the liquid composition, wherein the composition comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and wherein the solid composition is dissolvable or dispersible in an aqueous liquid solvent, and wherein the liquid composition comprises a concentration within a range from about 4 mg/mL to about 100 mg/mL of the active compound, or any pharmaceutically acceptable salt thereof.

Nebulizers are devices capable of aerosolizing liquids. Preferably, the nebulizer of the kit of the invention is selected from jet nebulizers, ultrasonic nebulizers, piezo-electronic nebulizers, jet collision nebulizers, electrohydrodynamic nebulizers, capillary force nebulizers, perforated membrane nebulizers and perforated vibrating membrane nebulizers (M. Knoch, M. Keller, *Expert Opin. Drug Deliv.,* 2005, 2, 377). Particularly preferred are piezoelectric, electrohydrodynamic and/or perforated membrane-type nebulizers, e.g. nebulizers from the drug delivery platforms Mystic™ (Battelle Pharma [Battelle Memorial Institute], United States), eFlow™ (Pari GmbH, Germany), Aeroneb™, Aeroneb Pro™, Aero Dose™ (Aerogen Inc, United States). These types of nebulizers are particularly useful if the aerosol is to be delivered to the bronchi and/or lungs.

Preferably, the nebulizer should be selected or adapted to be capable of aerosolizing the liquid composition at a rate of at least about 0.1 mL/min. More preferably, the nebulizer is capable of an (total) output rate (the rate at which the aerosol is emitted from the aerosol generator) of at least about 0.150 mL/min or at least about 150 mg/min for those liquid compositions the densities of which are—for practical purposes—close to 1 g/mL, i.e. within the range from about 0.95 g/mL to about 1.05 g/mL. In further embodiments, the output rate of the nebulizer is within the range from about 200 mg/min to about 700 mg/min, or from about 250 mg/min to about 650 mg/min, respectively.

The nebulizer should also preferably be selected or adapted to be capable of aerosolizing and emitting the liquid composition at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, per minute. The (mean) delivery rate of a drug or active compound is a parameter to determine the amount of drug or active compound a patient might be expected to receive during a treatment period. In further embodiments, the nebulizer is selected or adapted to enable a mean delivery rate of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, at the range from about 3 mg per minute to about 25 mg per minute or at the range from about 5 mg per minute to about 18 mg per minute, respectively.

According to a further preference, the nebulizer should be selected or adapted to be capable of aerosolizing and emitting at least of about 70 wt.-% of the loaded dose of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, whereas said fraction of the loaded dose is comprised of droplets having a mass median diameter of not more than about 5 μm. A fraction of a dispersed phase having a droplet size of not more than about 5 μm is often referred to as the respirable fraction, as droplets of said size—in contrast to larger droplets—have a high chance of being deposited in the lungs, instead of the trachea and the pharynx. More preferably, at least of about 80 wt.-% of the dose filled into the nebulizer is aerosolized to droplets of a size of not more than about 5 μm and emitted from the device. Such a device may be best selected by using an, optionally customized, electronic nebulizer based on the vibrating perforated membrane design, such as a nebulizer from the eFlow™ drug delivery platform (Pari GmbH, Germany). According to even more preferred embodiments, a least of about 85 wt.-% and about 90 wt.-%, respectively, of the loaded dose is aerosolized to droplets of a size of not more than about 5 μm and emitted.

In another aspect the invention provides a method of preparing and delivering an aerosol for pulmonary administration, said method comprising the steps of providing a liquid pharmaceutical composition comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in a concentration within a range from about 4 mg/mL to about 100 mg/mL, or providing a solid pharmaceutical composition for preparing the liquid composition, wherein the composition comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, and wherein the solid composition is dissolvable or dispersible in an aqueous liquid solvent, and wherein the liquid composition comprises a concentration within a range from about 4 mg/mL to about 100 mg/mL of the active compound, or any pharmaceutically acceptable salt thereof, and providing a nebulizer capable of aerosolizing said liquid pharmaceutical composition at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, per minute, the nebulizer being further adapted to emit an aerosol comprising a dispersed liquid phase having a mass median diameter from about 1.5 μm to about 5 μm, and having a droplet size distribution having a geometrical standard deviation from about 1.2 to about 1.7, and operating the nebulizer to aerosolize the liquid pharmaceutical composition.

The composition of the invention, whether liquid, initially solid or finally aerosolized, or the pharmaceutical kit comprising the composition, can be used for the prevention, management or treatment of diseases or conditions of the lungs being mediated by or resulting from human neutrophil elastase activity, e.g. pulmonary diseases, such as alpha-1 antitrypsin deficiency (AATD), cystic fibrosis (CF), non-cystic fibrosis bronchiactasis (NCFB), or chronic obstructive pulmonary disease (COPD), or infections of the lungs causing diseases or conditions of the lungs, being mediated by human neutrophil elastase activity.

As used herein, the term "prevention"/"preventing" e.g. preventive treatments comprise prophylactic treatments. In preventive applications, the pharmaceutical composition or the pharmaceutical aerosol of the invention is administered to a subject suspected of having, or at risk for developing diseases or conditions of the lungs being mediated by or resulting from human neutrophil elastase activity.

As used herein, the term "management" means increasing the time to appearance of a symptom of diseases or conditions of the lungs being mediated by or resulting from human neutrophil elastase activity or a mark associated with diseases or conditions of the lungs being mediated by or resulting from human neutrophil elastase activity or slowing the increase in severity of a symptom of diseases or conditions of the lungs being mediated by or resulting from human neutrophil elastase activity. Further, "management" as used herein includes reversing or inhibition of disease progression. "Inhibition" of disease progression or disease complication in a subject means preventing or reducing the disease progression and/or disease complication in the subject.

The terms "treatment"/"treating" as used herein includes: (1) delaying the appearance of clinical symptoms of the state, disease or condition developing in an animal, particularly a mammal and especially a human, that may be afflicted with or predisposed to the state, disease or condition but does not yet experience or display clinical or subclinical symptoms of the state, disease or condition; (2) inhibiting the state or condition (e.g. arresting, reducing or delaying the development of the disease, or a relapse thereof in case of maintenance treatment, of at least one clinical or subclinical symptom thereof; and/or (3) relieving the condition (i.e. causing regression of the state, disease or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

In therapeutic applications, the pharmaceutical composition is usually administered to a subject such as a patient already suffering from diseases or conditions of the lungs being mediated by or resulting from human neutrophil elastase activity, in an amount sufficient to cure or at least partially arrest the symptoms of the disease or condition. Amounts effective for this use will depend on the severity and course of the disease, previous therapy, the subject's health status and response to the drugs, and the judgment of the treating physician.

In the case wherein the subject's condition does not improve, the pharmaceutical composition or the pharmaceutical aerosol of the invention may be administered chronically, which is, for an extended period of time, including throughout the duration of the subject's life in order to ameliorate or otherwise control or limit the symptoms of the subject's disease or condition.

In the case wherein the subject's status does improve, the pharmaceutical composition or the pharmaceutical aerosol may be administered continuously; alternatively, the dose of drugs being administered may be temporarily reduced or temporarily suspended for a certain length of time (i.e., a "drug holiday").

Once improvement of the patient's condition has occurred, a maintenance dose of the pharmaceutical composition or the pharmaceutical aerosol of the invention is administered if necessary. Subsequently, the dosage or the frequency of administration, or both, is optionally reduced, as a function of the symptoms, to a level at which the improved disease is retained.

Thus in another aspect the invention provides a pharmaceutical composition comprising the active compound cyclo (-OctG-Glu-Thr-Ala-Ser-Ile-Pro-Pro-Gln-Lys-Tyr-$^{D}$Pro-Pro-), or any pharmaceutically acceptable salt thereof; wherein OctG is (S)-2-aminodecanoic acid; $^{D}$Pro is D-proline; and optionally one or more pharmaceutically acceptable diluents, excipients or carriers, for use in a method for the prevention, management or treatment of diseases or conditions of the lungs being mediated by or resulting from human neutrophil elastase activity in a subject, preferably for use in a method for treatment of diseases or conditions of the lungs being mediated by or resulting from human neutrophil elastase activity in a subject.

Also provided is the use of the pharmaceutical composition as described herein for the manufacture of a medicament for the prevention, management or treatment of diseases or conditions of the lungs being mediated by or resulting from human neutrophil elastase activity in a subject, preferably for the manufacture of a medicament for the treatment of diseases or conditions of the lungs being mediated by or resulting from human neutrophil elastase activity in a subject.

Also provided is the use of a pharmaceutical composition as described herein for the prevention, management or treatment of diseases or conditions of the lungs being mediated by or resulting from human neutrophil elastase activity in a subject, preferably for the treatment of diseases or conditions of the lungs being mediated by or resulting from human neutrophil elastase activity in a subject.

Also provided is a method for the prevention, management or treatment of diseases or conditions of the lungs being mediated by or resulting from human neutrophil elastase activity in a subject, preferably a method for the treatment of diseases or conditions of the lungs being mediated by or resulting from human neutrophil elastase activity in a subject, comprising administering to said subject a pharmaceutical composition as described herein e.g. administering to said subject a therapeutically effective amount of a pharmaceutical composition as described herein.

The term "pharmaceutically acceptable diluent, excipient or carrier" as used herein refers to a carrier or excipient or diluent that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

Determination of a therapeutically effective amount is well within the capability of those skilled in the art, especially in light of the detailed disclosure provided herein. In some embodiments, a therapeutically effective amount of the active compound or a pharmaceutically acceptable salt thereof, may (i) reduce the concentration of active elastase in sputum of a subject, ii) may inhibit the activity of human neutrophil elastase activity in sputum of a subject in various embodiments, the amount is sufficient to ameliorate, palliate, lessen, and/or delay one or more of symptoms of diseases or conditions of the lungs being mediated by or resulting from human neutrophil elastase activity in a subject.

The therapeutically effective amount may vary depending on the subject, and disease or condition being treated, the weight and age of the subject, the severity of the disease or condition, and the manner of administering, which can readily be determined by one ordinary skilled in the art.

In one embodiment the diseases or conditions of the lungs being mediated by or resulting from human neutrophil elastase activity are pulmonary diseases such as alpha-1 antitrypsin deficiency (AATD), cystic fibrosis (CF), non-cystic fibrosis bronchiactasis (NCFB), or chronic obstructive pulmonary disease (COPD), or infections of the lungs causing diseases or conditions of the lungs, being mediated by human neutrophil elastase activity.

In a preferred embodiment the diseases or conditions of the lungs being mediated by or resulting from human neutrophil elastase activity are pulmonary diseases, wherein the pulmonary disease is non-cystic fibrosis bronchiactasis (NCFB) or cystic fibrosis (CF).

In a more preferred embodiment the diseases or conditions of the lungs being mediated by or resulting from human neutrophil elastase activity are pulmonary diseases, wherein the pulmonary disease is cystic fibrosis (CF).

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, is administered to the subject as pharmaceutical aerosol for pulmonary administration comprising a dispersed liquid phase and a continuous gas phase, wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-);

or any pharmaceutically acceptable salt thereof; wherein

OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7.

Preferably the aerosol being emitted from an aerosol generator at a rate of at least about 0.1 mL dispersed liquid phase per minute.

Equally preferably the aerosol being emitted from an aerosol generator at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-); or any pharmaceutically acceptable salt thereof; per minute.

The aerosol is preferably emitted from an aerosol generator at a rate and at a mean delivery rate as described in the preferred embodiments above.

In one embodiment the pharmaceutical composition for use in a method for the prevention, management or treatment of diseases or conditions of the lungs being mediated by or resulting from human neutrophil elastase activity in a subject, is a liquid pharmaceutical composition for preparing an aerosol as described herein, wherein the liquid pharmaceutical composition comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, in a concentration within a range from about 4 mg/mL to about 100 mg/mL, preferably, within a range from about 17 mg/mL to about 95 mg/mL, or about 35 mg/mL to about 95 mg/mL, respectively, and more preferably, within a range from about 70 mg/mL to about 95 mg/mL.

In another aspect the invention provides a pharmaceutical aerosol for pulmonary administration comprising a dispersed liquid phase and a continuous gas phase, wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-); or any pharmaceutically acceptable salt thereof; wherein OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7, for use in a method for the prevention, management or treatment of diseases or conditions of the lungs being mediated by or resulting from human neutrophil elastase activity in a subject.

The aerosol is preferably emitted from an aerosol generator at a rate and at a mean delivery rate as described in the preferred embodiments above.

Also provided is the use of the pharmaceutical aerosol as described herein for the manufacture of a medicament for the prevention, management or treatment of diseases or conditions of the lungs being mediated by or resulting from human neutrophil elastase activity in a subject, preferably for the manufacture of a medicament for the treatment of diseases or conditions of the lungs being mediated by or resulting from human neutrophil elastase activity in a subject.

Also provided is the use of the pharmaceutical aerosol as described herein for the prevention, management or treatment of diseases or conditions of the lungs being mediated by or resulting from human neutrophil elastase activity in a subject, preferably for the treatment of diseases or conditions of the lungs being mediated by or resulting from human neutrophil elastase activity in a subject.

Also provided is a method for the prevention, management or treatment of diseases or conditions of the lungs being mediated by or resulting from human neutrophil elastase activity in a subject, preferably a method for the treatment of diseases or conditions of the lungs being mediated by or resulting from human neutrophil elastase activity in a subject, comprising administering to said subject the pharmaceutical aerosol as described herein e.g. administering to said subject a therapeutically effective amount of a pharmaceutical aerosol as described herein.

In one embodiment the diseases or conditions of the lungs being mediated by or resulting from human neutrophil elastase activity are pulmonary diseases such as alpha-1 antitrypsin deficiency (AATD), cystic fibrosis (CF), non-cystic fibrosis bronchiactasis (NCFB), or chronic obstructive pulmonary disease (COPD), or infections of the lungs causing diseases or conditions of the lungs, being mediated by human neutrophil elastase activity.

In a preferred embodiment the diseases or conditions of the lungs being mediated by or resulting from human neutrophil elastase activity are pulmonary diseases, wherein the pulmonary disease is non-cystic fibrosis bronchiactasis (NCFB) or cystic fibrosis (CF).

In a more preferred embodiment the diseases or conditions of the lungs being mediated by or resulting from human neutrophil elastase activity are pulmonary diseases, wherein the pulmonary disease is cystic fibrosis (CF).

The counter ion of the active compound of the pharmaceutical composition or the pharmaceutical aerosol for use in a method for the prevention, management or treatment of diseases or conditions of the lungs being mediated by or resulting from human neutrophil elastase activity in a subject is as described for the active compound above and is preferably acetate.

The pharmaceutical composition or the pharmaceutical aerosol for use in a method for the prevention, management or treatment of diseases or conditions of the lungs being mediated by or resulting from human neutrophil elastase activity in a subject is usually administered to the subject by oral inhalation or intratracheal, preferably by oral inhalation.

The dosing regimen of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, comprised by the pharmaceutical composition or the pharmaceutical aerosol, in the methods provided herein may vary depending upon the indication, route of administration, and severity of the condition, for example. Depending on the route of administration, a suitable dose can be calculated according to body weight, body surface area, or organ size. Additional factors that can be taken into account include time and frequency of administration, drug combinations, reaction sensitivities, and tolerance/response to therapy. The amount, e.g. the therapeutically effective amount of the active compound cyclo(-OctG-Glu-Thr-Ala-Ser-Ile-Pro-Pro-Gln-Lys- Tyr-$^{D}$Pro-Pro-), or a pharmaceutically acceptable salt thereof, may be provided in a single dose or multiple doses to achieve the desired treatment endpoint.

The frequency of dosing will depend on the pharmacokinetic parameters of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, administered, the route of administration, and the particular disease treated. The dose and frequency of dosing may also depend on pharmacokinetic and pharmacodynamic, as well as toxicity and therapeutic efficiency data. For example, pharmacokinetic and pharmacodynamic information about the active compound or a pharmaceutically acceptable salt thereof, can be collected through preclinical in vitro and in vivo studies, later confirmed in humans during the course of clinical trials. Thus, for the active compound or a pharmaceutically acceptable salt thereof, used in the methods provided herein, a therapeutically effective dose can be estimated initially from biochemical and/or cell-based assays. Then, dosage can be formulated in animal models to achieve a desirable circulating concentration range. As human studies are conducted further information will emerge regarding the appropriate dosage levels and duration of treatment for various diseases and conditions.

Toxicity and therapeutic efficacy of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the ED50 with little or no toxicity.

An exemplary treatment regime entails administration once daily, twice daily, three times daily, every day, every second day, every third day, every fourth day, every fifth day, every sixth day, twice per week, once per week. The active compound cyclo(-OctG-Glu-Thr-Ala-Ser-Ile-Pro-Pro-Gln-Lys-Tyr-$^{D}$Pro-Pro-), or any pharmaceutically acceptable salt thereof, is usually administered on multiple occasions. Intervals between single dosages can be, for example, less than a day, a day, two days, three days, four days, five days, six days or a week. The combination of the invention may be given as a continuous uninterrupted treatment. The combination of the invention may also be given in a regime in which the subject receives cycles of treatment (administration cycles) interrupted by a drug holiday or period of non-treatment.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose between about 0.1 and about 10000 mg/day.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is is administered to the subject at a dose between about 0.001 and about 100 mg/kg.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose between about 5 and about 1000 mg/day.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose between about 20 and about 960 mg/day.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose between about 80 and about 320 mg/day.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose of about 20, about 60, about 120, about 240, about 480 or about 960 mg/day.

In one embodiment the active compound cyclo(-OctG-Glu-Thr-Ala-Ser-Ile-Pro-Pro-Gln-Lys-Tyr-$^{D}$Pro-Pro-), or any pharmaceutically acceptable salt thereof, of the pharmaceutical composition or the pharmaceutical aerosol for use in a method for the prevention, management or treatment of diseases or conditions of the lungs being mediated by or resulting from human neutrophil elastase activity in a subject is administered to the subject at a dose of about 80, about 160, or about 320 mg/day.

In another aspect the invention provides a kit for the preparation and delivery of a pharmaceutical aerosol for pulmonary administration comprising a dispersed liquid phase and a continuous gas phase, wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-);

or any pharmaceutically acceptable salt thereof; wherein OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7;

and wherein the kit comprises a nebulizer and a liquid composition comprising a concentration within a range from about 4 mg/mL to about 100 mg/mL of the active compound; or any pharmaceutically acceptable salt thereof;

or comprises a nebulizer and a solid pharmaceutical composition for preparing the liquid composition, wherein the composition comprises the active compound cyclo(-OctG-Glu-Thr-Ala-Ser-Ile-Pro-Pro-Gln-Lys-Tyr-$^{D}$Pro-Pro-); or any pharmaceutically acceptable salt thereof; and wherein the solid composition is dissolvable or dispersible in an aqueous liquid solvent, and wherein the liquid composition comprises a concentration within a range from about 4 mg/mL to about 100 mg/mL of the active compound; or any pharmaceutically acceptable salt thereof, for use in a method for the prevention, management or treatment of diseases or conditions of the lungs being mediated by or resulting from human neutrophil elastase activity in a subject.

Also provided is the use of the kit as described herein for the manufacture of a medicament for the prevention, management or treatment of diseases or conditions of the lungs being mediated by or resulting from human neutrophil elastase activity in a subject, preferably for the manufacture of a medicament for the treatment of diseases or conditions of the lungs being mediated by or resulting from human neutrophil elastase activity in a subject.

Also provided is the use of the kit as described herein for the prevention, management or treatment of diseases or conditions of the lungs being mediated by or resulting from human neutrophil elastase activity in a subject, preferably for the treatment of diseases or conditions of the lungs being mediated by or resulting from human neutrophil elastase activity in a subject.

Also provided is a method for the prevention, management or treatment of diseases or conditions of the lungs being mediated by or resulting from human neutrophil elastase activity in a subject, preferably a method for the treatment of diseases or conditions of the lungs being mediated by or resulting from human neutrophil elastase activity in a subject, comprising administering to said subject the pharmaceutical aerosol of the kit as described herein e.g. administering to said subject a therapeutically effective amount of a pharmaceutical aerosol of the kit as described herein.

In one embodiment the nebulizer of the kit for use in a method for the prevention, management or treatment of diseases or conditions of the lungs being mediated by or resulting from human neutrophil elastase activity in a subject is selected from the group consisting of jet nebulizers, ultrasonic nebulizers, piezoelectronic nebulizers, jet collision nebulizers, electrohydrodynamic nebulizers, capillary force nebulizers, perforated membrane nebulizers and perforated vibrating membrane nebulizers.

In one embodiment the nebulizer of the kit for use in a method for the prevention, management or treatment of diseases or conditions of the lungs being mediated by or resulting from human neutrophil elastase activity in a subject is adapted to be capable of aerosolizing the liquid composition at a rate of at least about 0.8 mg of the active compound cyclo(-OctG-Glu-Thr-Ala-Ser-Ile-Pro-Pro-Gln-Lys-Tyr-$^{D}$Pro-Pro-); or any pharmaceutically acceptable salt thereof; per minute.

In one embodiment at least about 70 wt.-% of the loaded dose of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, comprised by the kit is comprised of droplets having a mass median diameter of not more than about 5 μm.

In one embodiment the counter ion of the active compound comprised by the kit is as described for the active compound above and is preferably acetate.

In another aspect the invention provides a kit comprising the active compound cyclo(-OctG-Glu-Thr-Ala-Ser-Ile-Pro-Pro-Gln-Lys-Tyr-$^{D}$Pro-Pro-), or any pharmaceutically acceptable salt thereof; wherein OctG is (S)-2-aminodecanoic acid;

$^{D}$Pro is D-proline;

and a package insert wherein the package insert comprises instructions for treating a subject for diseases or conditions of the lungs being mediated by or resulting from human neutrophil elastase activity using the active compound.

In one embodiment the kit comprises the active compound cyclo(-OctG-Glu-Thr-Ala-Ser-Ile-Pro-Pro-Gln-Lys-Tyr-$^{D}$Pro-Pro-), or any pharmaceutically acceptable salt thereof, as aerosol for pulmonary administration comprising a dispersed liquid phase and a continuous gas phase, wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-); or any pharmaceutically acceptable salt thereof;

(b) has a mass median diameter from about 1.5 μm to about 5 μm; and (c) has a droplet size distribution having a geometrical standard deviation from about 1.2 to about 1.7.

In one embodiment at least about 70 wt.-% of the loaded dose of the active compound cyclo(-OctG-Glu-Thr-Ala-Ser-Ile-Pro-Pro-Gln-Lys-Tyr-$^{D}$Pro-Pro-), or any pharmaceutically acceptable salt thereof, comprised by the kit is comprised of droplets having a mass median diameter of not more than about 5 μm.

In one embodiment the counter ion of the active compound comprised by the kit is as described for the active compound above and is preferably acetate.

The following Examples illustrate the present invention but are not to be construed as limiting its scope in any way.

EXAMPLES

Example 1

248.18 g of acetate salt of cyclo(-OctG-Glu-Thr-Ala-Ser-Ile-Pro-Pro-Gln-Lys-Tyr-$^{D}$Pro-Pro-) based on a net peptide content of 93.03% (see calculation below) and corresponding to 230.88 g of net peptide, were dissolved in 0.5% (w/w) aqueous sodium chloride solution. The solution was adjusted to pH 5.5 with 154 g 1 M sodium hydroxide and finally 0.5% (w/w) aqueous sodium chloride solution was added to a total weight of 2957 g. After sterile filtration through 2×0.22 μm pore size filters the product was packed in Ph.Eur. Type 1 glass vials with fluoropolymer coated bromobutyl rubber stoppers and tear-off plain aluminium overseals. The strength of the solution was 80 mg/mL.

Calculation of the net peptide content of the drug substance (active compound):

$$\text{Net peptide content [\%]}=[(100-\text{impurity [\%]}/100)\times(100-\text{water content [\%]}/100)\times(100-\text{residual solvent [\%]}/100)\times(100-\text{residual } \mathit{TFA}/100)\times\text{free salt [\%]}/100]\times 100=[(100-0.7/100)\times(100-2.5/100)\times(100-0.013/100)\times 96.1/100]\times 100=93.03\%$$

Example 2

The formulation of Example 2 was prepared as described in Example 1 except 0.6% (w/w) aqueous sodium chloride solution was used.

Example 3

4.2 g of acetate salt of cyclo(-OctG-Glu-Thr-Ala-Ser-Ile-Pro-Pro-Gln-Lys-Tyr-$^{D}$Pro-Pro-) corrected for 95% purity were dissolved in 40 mL 0.6% (w/w) aqueous sodium chloride solution. The solution was adjusted to pH 5.5 with 1 M sodium hydroxide and finally 0.6% (w/w) sodium chloride solution was added to a total volume of 50 mL. After sterile filtration under aseptic conditions (laminar air flow) using an PES (Polyethersulfone) 0.2 μm syringe filter the formulation was aliquoted into sterile 5 mL vials with sterile teflon coated rubber stoppers and stored refrigerated at 5±3° C. and room temperature (25±2° C.), respectively. The strength of the solution was 80 mg/mL. During 12 weeks the solution was observed for stability. Physicochemical parameters (Table 1) and aerosol characteristics (Table 2) of an aerosol prepared and delivered by an eFlow® 30 XL electronic nebulizer (Pari Pharma GmbH, Starnberg, Germany) were determined at the beginning and at the end of the observation period. Physicochemical characterization and determination of aerosol characteristics (laser diffraction with Malvern Mastersizer X, V2.15, [Malvern Instruments GmbH, Herrenberg, Germany]), were performed by Pari Pharma GmbH, BU Pharma, Gräfeling, Germany, according to pharmacopoeia-compliant methods.

TABLE 1

Physiochemical properties of formulation of Example 3

| Example 3 | Initial | After 12 weeks at 5° C. | After 12 weeks at 25° C. |
|---|---|---|---|
| pH | 5.5 | 5.4 | 5.4 |
| Osmolality [mOsmol/kg] | 353 | 355 | 356 |
| Viscosity [mPa * s] | 1.44 | 1.41 | 1.41 |
| Surface tension [mN/m] | 50.0 | 50.3 | 50.2 |

The physicochemical properties of the above formulation remain unchanged during 12 weeks at 5° C. and 25° C., respectively.

TABLE 2

Aerosol characteristics of formulation of Example 3, determined in triplicate

| Example 3 | Initial | After 12 weeks at 5° C. | After 12 weeks at 25° C. |
|---|---|---|---|
| Mass median diameter [μm] | 3.00 ± 0.12 | 2.89 ± 0.05 | 2.92 ± 0.04 |
| Geometric standard deviation | 1.55 ± 0.03 | 1.53 ± 0.01 | 1.54 ± 0.01 |
| Respirable fraction <5 μm [%] | 86.18 ± 2.52 | 88.60 ± 1.14 | 78.91 ± 0.61 |
| Total output rate [mg/min] | 338 ± 25 | 304 ± 9 | 320 ± 10 |

During storage of 12 weeks at 5° C. and 25° C., respectively, no significant (P=95%, n=3) changes in mass median diameter, geometric standard deviation and respirable fraction (<5 μm) were observed. Only the total output rate of the 5° C. sample was slightly decreased.

Example 4

1.05 g of acetate salt of cyclo(-OctG-Glu-Thr-Ala-Ser-Ile-Pro-Pro-Gln-Lys-Tyr-$^{D}$Pro-Pro-) corrected for 95% purity were dissolved in 0.9% (w/w) aqueous sodium chloride solution to obtain a total volume of 10 mL. The strength of the solution was 100 mg/mL. Physicochemical parameters (Table 3) and aerosol characteristics (Table 4) of an aerosol prepared and delivered by an eFlow® 30 XL electronic nebulizer were determined by Pari Pharma GmbH, BU Pharma, Gräfeling, Germany, as explained above.

TABLE 3

Physiochemical properties of formulation of Example 4

| | Example 4 |
|---|---|
| pH | 4.32 |
| Osmolality [mOsmol/kg] | 433 |
| Viscosity [mPa * s] | 1.62 |
| Surface tension [mN/m] | 49.8 |

TABLE 4

Aerosol characteristics of formulation of Example 4, determined in triplicate

| | Example 4 |
|---|---|
| Mass median diameter [μm] | 3.31 ± 0.10 |
| Geometric standard deviation | 1.55 ± 0.02 |
| Respirable fraction <5 μm [%] | 81.75 ± 2.33 |
| Total output rate [mg/min] | 549.7 ± 21.3 |

Example 5

1.05 g of acetate salt of cyclo(-OctG-Glu-Thr-Ala-Ser-Ile-Pro-Pro-Gln-Lys-Tyr-$^{D}$Pro-Pro-) corrected for 95% purity were dissolved in 0.9% (w/w) aqueous sodium chloride solution to obtain a total volume of 10 mL. 0.02% (w/w) Polysorbate 80 were added subsequently. The strength of the solution was 100 mg/mL. Physicochemical parameters (Table 5) and aerosol characteristics (Table 6) of an aerosol prepared and delivered by an eFlow® 30 XL electronic nebulizer were determined by Pari Pharma GmbH, BU Pharma, Gräfeling, Germany, as explained above.

TABLE 5

Physiochemical properties of formulation of Example 5

| | Example 5 |
|---|---|
| pH | 4.44 |
| Osmolality [mOsmol/kg] | 435 |
| Viscosity [mPa * s] | 1.55 |
| Surface tension [mN/m] | 48.6 |

TABLE 6

Aerosol characteristics of formulation of Example 5, determined in triplicate

| | Example 5 |
|---|---|
| Mass median diameter [μm] | 2.77 ± 0.02 |
| Geometric standard deviation | 1.51 ± 0.01 |
| Respirable fraction <5 μm [%] | 91.19 ± 0.56 |
| Total output rate [mg/min] | 273.7 ± 3.5 |

Example 6a-e 5.4 g of acetate salt of cyclo(-OctG-Glu-Thr-Ala-Ser-Ile-Pro-Pro-Gln-Lys-Tyr-$^{D}$Pro-Pro-) based on a net peptide content of 93.03% (see calculation above) and corresponding to 5.023 g of net peptide, were dissolved in 0.5% (w/w) aqueous sodium chloride solution. The solution was adjusted to pH 5.5 with 1 M sodium hydroxide and finally 0.5% (w/w) sodium chloride solution was added to a total volume of 71.8 mL. The strength of the solution was 70 mg/mL (Example 6a).

Diluted solutions with strengths of 35 mg/mL (Example 6b), 17.4 mg/mL (Example 6c), 8.8 mg/mL (Example 6d) and 4.3 mg/mL (Example 6e) were prepared with placebo (0.5% [w/w] aqueous sodium chloride solution) according to Table 7.

TABLE 7

Preparation scheme for diluted solutions of Examples 6b, 6c, 6d and 6e

| Aliqot of 70 mg/mL formulation [mL] | Amount of placebo [mL] | Final strength of diluted solution [mg/mL] | pH of diluted solutions[a)] |
|---|---|---|---|
| 10 | 10 | 35 | 5.46 |
| 10 | 30 | 17.4 | 5.43 |
| 2.5 | 17.5 | 8.8 | 5.42 |
| 2.5 | 37.5 | 4.3 | 5.40 |

[a)]The pH of the placebo used for the dilution step was 4.76 and the pH of the corresponding diluted solution was not re-adjusted to pH 5.5.

Example 6f

The formulation of Example 6f was prepared according to the procedure described in Example 1. The strength of the solution was 80 mg/mL.

Determination of Delivery Rates (Mean) and Total Delivered Doses of Examples 6a, 6c, 6e and 6f The determination of delivery rates and total delivered doses was performed by Intertek Melbourn Scientific (Melbourn, UK) in triplicate for 70 mg/mL (Example 6a), 17.4 mg/mL (Example 6c) and 4.3 mg/mL (Example 6e) formulations, and in quintuplicate for the 80 mg/mL (Example 6f) formulation using Pari eFlow® XL 30 devices (Pari Pharma, Starnberg, Germany) and a suitable, pharmacopoeia-compliant method for said determination of formulations comprising acetate salt of cyclo(-OctG-Glu-Thr-Ala-Ser-Ile-Pro-Pro-Gln-Lys-Tyr-$^{D}$Pro-Pro-).

The results (mean values) are summarized in Table 8.

TABLE 8

Delivery rates and total delivered doses of Examples 6a, 6c, 6e and 6f

| Example | 6f | 6a | 6c | 6e |
|---|---|---|---|---|
| Strength of solution [mg/mL] | 80 | 70 | 17.4 | 4.3 |
| Delivered mass (mean) [g] | 0.7566 | 3.7202 | 3.7402 | 3.7928 |
| Mean delivery rate [mg/min] | 8.0 | 8.1 | 3.2 | 0.8 |
| Mean of total delivered active compound [mg] | 32.1 | 131.7 | 25.9 | 8.2 |
| Mean efficiency[a)] [%] | 53.0 | 50.6 | 39.8 | 50.3 |

[a)]Mean efficiency [%] is mean of total delivered active compound (dose, actual)/mean of theoretical dose delivered (calculated by using delivered mass (mean) and strength of solution, density assumed to be 1 g/mL)

Aerodynamic Particle Size Distribution (APSD) Determination of Examples 6a, 6c, 6e and 6f The APSD determination was performed by Intertek Melbourn Scientific (Melbourn, UK) in triplicate for 70 mg/mL (Example 6a), 17.4 mg/mL (Example 6c) and 4.3 mg/mL (Example 6e) formulations, and in quintuplicate for the 80 mg/mL (Example 6f) formulation using the Next Generation Impactor (NGI), Pari eFlow® XL 30 devices (Pari Pharma, Starnberg, Germany) and a suitable, pharmacopoeia-compliant method for the APSD of formulations comprising acetate salt of cyclo(-OctG-Glu-Thr-Ala-Ser-Ile-Pro-Pro-Gln-Lys-Tyr-$^{D}$Pro-Pro-).

The results (mean values) are summarized in Table 9.

TABLE 9

Aerodynamic particle size distribution determination (APSD) of Examples 6a, 6c, 6e and 6f

| Example | 6f | 6a | 6c | 6e |
|---|---|---|---|---|
| Strength of solution [mg/mL] | 80 | 70 | 17.4 | 4.3 |
| NGI Stages | | | | |
| Throat [mg] | 0.62 | 1.39 | 0.50 | 0.12 |
| Stage 1 [mg] | 0.90 | 3.20 | 1.01 | 0.24 |
| Stage 2 [mg] | 0.80 | 2.98 | 1.02 | 0.24 |
| Stage 3 [mg] | 4.80 | 21.44 | 7.14 | 1.82 |
| Stage 4 [mg] | 25.18 | 115.92 | 29.08 | 7.30 |
| Stage 5 [mg] | 24.18 | 92.74 | 20.25 | 4.36 |
| Stage 6 [mg] | 6.82 | 16.64 | 5.33 | 1.27 |
| Stage 7 [mg] | 1.17 | 4.76 | 1.32 | 0.31 |
| MOC[a)] [mg] | 0.18 | 0.23 | 0.04 | 0.01 |
| Sum [mg] | 64.64 | 259.29 | 65.69 | 15.66 |
| Delivered mass [g] | 0.87 | 3.96 | 4.04 | 3.92 |
| FPD[b),f)] ≤ 5 μm [mg] | 55.1 | 218.8 | 52.8 | 12.4 |
| FPD/Delivered mass [mg/g] | 63.3 | 55.2 | 13.1 | 3.2 |
| FPF[c),f)] ≤ 5 μm [%] | 85.2 | 84.4 | 80.4 | 79.3 |
| GSD[d),f)] | 1.5 | 1.4 | 1.5 | 1.4 |
| MMAD[e),f)] [μm] | 3.3 | 3.5 | 3.6 | 3.7 |

[a)]MOC: Micro-Orifice Collector
[b)]FPD: Fine Particle Dose
[c)]FPF: Fine Partice Fraction; FPF is the FPD expressed as a percentage of the delivered dose
[d)]GSD: Geometric Standard Deviation
[e)]MMAD: Mass Median Aerodynamic Distribution
[f)]After determination of the amount of drug (active compound) deposited on the various stages FPD; FPF, GSD and MMAD were calculated using the CITAS program, version 3.10.

From the results above, no significant changes were seen in the performance of the solutions of different strength within the presented range, except the effect of the reduced concentration on the drug totals.

GLP-Compliant 28-Day Inhalation Toxicity Study in Rats

In a GLP-compliant 28-day inhalation toxicity study in rats, conducted by Charles River Laboratories Preclinical Services, Tranent, Edinburgh, UK, the formulation described in Example 2 and dilutions thereof as well as the vehicle were administered using the Pari eFlow® XL 30 nebulizer device (Pari Pharma, Starnberg, Germany) for 100 min per day for 28 days, followed by a 2-week recovery period. Rats were treated with vehicle (0.6% [w/w] aqueous sodium chloride solution adjusted to pH 5.5 with 1 M HCl pharmaceutical grade) or aerosols containing 0.15, 0.73 and 1.63 mg/L of cyclo(-OctG-Glu-Thr-Ala-Ser-Ile-Pro-Pro-Gln-Lys-Tyr-$^{D}$Pro-Pro-), corresponding to overall mean group achieved drug doses of 0, 11, 53 and 119 mg/kg/day, respectively. Ten animals were used for the main toxicity study, and 5 additional animals for the recovery phase. Parameters assessed included clinical signs, body weights, food consumption, ophthalmic examination, clinical pathology, gross necropsy findings, organ weights and histopathologic examinations. Slightly reduced body weight gain was observed in males at 119 mg/kg/day compared to the vehicle control group. This was associated with reduction in food consumption in treated animals. There was a good recovery in body weight gain during the recovery period between day 28 and 42. There were no clinical signs or ophthalmic findings.

There were no findings in clinical pathology (haematology, coagulation, clinical chemistry and urinalysis investigations) which were considered toxicologically relevant. There were no treatment-related changes in organ weights or gross findings following treatment with the drug. Histopathology of the larynx revealed focal minimal squamous metaplasia without cellular atypia of dysplasia in all groups. These changes resolved during the recovery period and were considered a non-adverse, adaptive response to mild irritation. Histopathology of the lungs revealed minimal to moderate multifocal alveolar macrophage accumulation in all groups. This slight increase in macrophage accumulation was considered a nonspecific response to the inhalation of high concentrations of material exceeding the clearance capacity of the lung. In conclusion, the No Observed Adverse Effect Level (NOAEL) was 119 mg/kg/day since the changes in body weight gain and food intake and the histopathologic findings in the larynx were considered non-adverse.

GLP-Compliant 28-Day Inhalation Toxicity Study in Monkeys

In a GLP-compliant 28-day inhalation toxicity study in cynomolgus monkeys, conducted by Charles River Laboratories Preclinical Services, Tranent, Edinburgh, UK, the formulation described in Example 2 and dilutions thereof as well as the vehicle were administered using the Pari eFlow® XL 30 nebulizer device (Pari Pharma, Starnberg, Germany) with an oro-nasal inhalation mask for 60 min per day for 28 days, followed by a 2-week recovery period. Monkeys were treated with vehicle (0.6% [w/w] aqueous sodium chloride solution adjusted to pH 5.5 with 1 M HCl pharmaceutical grade) or aerosolized acetate salt of cyclo(-OctG-Glu-Thr-Ala-Ser-Ile-Pro-Pro-Gln-Lys-Tyr-$^D$Pro-Pro-) corresponding to estimated mean achieved drug doses of 0, 11.2, 30.1 and 112 mg/kg/day, respectively. In total five males and five females were used for each dose of the toxicity study including recovery. Parameters assessed included clinical signs, body weights, electrocardiology, ophthalmic examination, clinical pathology, toxicokinetic parameters in the plasma, gross necropsy findings, organ weights and histopathologic examinations. There were no body weight changes, clinical signs, ophthalmic or electrocardiographic findings or changes in urinary parameters attributable to drug treatment. In haematology and clinical pathology, some minor, toxicologically insignificant changes were observed. None of these findings was considered toxicologically important, as the magnitude of responses was small, and most findings were confined to one sex and/or showed evidence of regression when both sexes were affected. Gross findings included increased lung weight in males at 112 mg/kg/day, and one animal with a mottled appearance of the lungs and enlarged tracheobronchial lymph node. Histopathologic findings were observed at all drug dose levels, including increased numbers of alveolar macrophages, perivascular/peribronchiolar infiltrates, and granular eosinophilic deposits in the lung and lymphoid hyperplasia in the tracheobronchial lymph nodes, which showed complete recovery. These findings demonstrated full reversibility during recovery, and were considered to be due to inhalation of material exceeding normal lung clearance capacity, particularly at 112 mg/kg/day. In conclusion, NOAEL in this study was 112 mg/kg/day, since the changes discussed above were all considered non-adverse.

First-in-Man Study in Healthy Subjects to Investigate Safety and Tolerability of Orally Inhaled Single Doses of a Formulation of Acetate Salt of cyclo(-OctG-Glu-Thr-Ala-Ser-Ile-Pro-Pro-Gln-Lys-Tyr-$^D$Pro-Pro-)

In this randomised, double-blind, placebo-controlled, parallel-group (per dose level) dose-escalation study of inhaled single doses in 48 healthy subjects in six dose groups of eight subjects each, conducted by Inamed GmbH, Gauting, Germany, the controlled oral inhalation of the formulation described in Example 1 and dilutions thereof as well as the placebo (0.5% [w/w] aqueous sodium chloride solution adjusted to pH 5.5 with 1 M HCl pharmaceutical grade) occurred via the Pari eFlow® XL 30 nebulizer device (Pari Pharma GmbH, Starnberg, Germany). The dose levels and corresponding concentrations of cyclo(-OctG-Glu-Thr-Ala-Ser-Ile-Pro-Pro-Gln-Lys-Tyr-$^D$Pro-Pro-) (active compound) are summarized in Table 10.

TABLE 10

| Dose | Preparation and Volume of nebulizer solution | Concentration |
|---|---|---|
| Dose Level 1 | 20 mg of drug in 4 mL solution | 5 mg/mL |
| Dose Level 2 | 60 mg of drug in 4 mL solution | 15 mg/mL |
| Dose Level 3 | 120 mg of drug in 4 mL solution | 30 mg/mL |
| Dose Level 4 | 240 mg of drug in 4 mL solution | 60 mg/mL |
| Dose Level 5 | 480 mg of drug in 6 mL solution | 80 mg/mL |
| Dose Level 6 | 960 mg of drug in 12 mL solution | 80 mg/mL |

The volume of placebo nebulizer solution corresponded to that of the active compound at a particular dose level. The duration of inhalation depended on the total volume of nebulizer solution and ranged between several minutes and roughly one hour. Adverse events were tabulated and summarized according to the current version of Medical Dictionary for Regulatory Activities.

Safety and Tolerability Results

No death, no serious adverse events (AE) and no other significant AE occurred during the study. In total, 27 AEs, thereof 24 treatment-emergent adverse events (TEAEs) were recorded in 13 subjects (27.1%). All of these subjects were on active compound. No AE was reported for subjects having inhaled placebo solution. Regarding the number of AEs as well as their intensity and causal relationship to the study medication, a higher total number of AEs and related AEs were reported from the group inhaling the highest dose of active compound (960 mg; dose group 6) when compared to the other dose levels. The majority of AEs and symptoms reported were related to the respiratory system, such as 'cough', 'respiratory tract irritation', increased mucus production or a transient decline in forced expiratory volume in the first second ($FEV_1$). The higher occurrence of respiratory symptoms and respiratory AEs, especially in the groups inhaling higher doses of active compound, may possibly have been related to the long duration of inhalation. These AEs may not necessarily have been related to the formulation of Example 1 and dilutions thereof itself, but may possibly be procedural AEs. Regarding the local tolerability, there were three inhalation-related adverse events ('cough'). The overall tolerability was judged as 'very good' or 'good' by the majority of subjects (97.9%). Throughout the study, the majority of the clinical laboratory values remained within the respective reference ranges. Most of the individual results of physical examination, vital-signs measurements, electrocardiogram (ECG) recordings and lung-function results were within the commonly accepted clinical reference ranges. No time-dependent influence of active compound on safety parameters measured became obvious. There was no relevant difference between the different dose groups.

The above presented results of the First-in-Man study show that the formulation of Example 1 and dilutions thereof are highly suitable for aerosolization in a wide range of concentrations and applicable for inhalation administration in humans even at high concentrations (80 mg/mL).

Effect of Inhalation Administration of Acetate Salt of Cyclo (-OctG-Glu-Thr-Ala-Ser-Ile-Pro-Pro-Gln-Lys-Tyr-$^D$Pro-Pro-) in an In Vivo Model of Neutrophil Activation in the Rat The purpose of this study (conducted by Envigo CRS Limited, Alconbury, Huntingdon, United Kingdom) was to evaluate the effects of acetate salt of cyclo(-OctG-Glu-Thr-Ala-Ser-Ile-Pro-Pro-Gln-Lys-Tyr-$^D$Pro-Pro-) administered by inhalation in a LPS/fMLP model of neutrophil activation in the rat.

Preparation of Formulations

The formulation for test animal group 1 (vehicle) was 0.5% (w/v) saline adjusted to a pH of 5.5 with 1 M HCl and filtered through a 0.2 μm filter.

The formulations for test animal groups 2-4 were prepared as follows:

The appropriate amount of acetate salt of cyclo(-OctG-Glu-Thr-Ala-Ser-Ile-Pro-Pro-Gln-Lys-Tyr-$^D$Pro-Pro-) was weighed and the appropriate amount of 0.5% (w/v) saline, pH 5.5, was added to produce a formulated concentration of 83.28 mg/mL. The pH of the final solution was adjusted to 5.5 with 1 M NaOH.

An appropriate amount of 83.28 mg/mL of acetate salt of cyclo(-OctG-Glu-Thr-Ala-Ser-Ile-Pro-Pro-Gln-Lys-Tyr-$^D$Pro-Pro-) was added to an appropriate amount of vehicle to produce a formulation of 15.62 mg/mL.

Finally, an appropriate amount of 15.62 mg/mL of acetate salt of cyclo(-OctG-Glu-Thr-Ala-Ser-Ile-Pro-Pro-Gln-Lys-Tyr-$^D$Pro-Pro-) was added to an appropriate amount of vehicle to produce a formulation of 5.21 mg/mL. The three formulation solutions (83.28 mg/mL, 15.62 mg/mL, 5.21 mg/mL) were then filtered through a 0.2 μm filter.

The formulations were prepared 1 day prior to dosing and stored at 2-8° C. in the dark until the day of use when they were removed from the fridge and maintained at room temperature (≤25° C.) and gently shaken for at least 1 h prior to dosing.

Table 11 summarizes the concentrations of the prepared formulations for test animal groups 1-4 taking into account a ratio of acetate salt/free base of cyclo(-OctG-Glu-Thr-Ala-Ser-Ile-Pro-Pro-Gln-Lys-Tyr-$^D$Pro-Pro-) being 1.041. Thus, these formulations correspond to the formulation described in Example 1 and dilutions thereof.

TABLE 11

| Group | Nominal concentration of drug | Formulated concentration of drug |
|---|---|---|
| 1 (control) | 0 mg/mL | 0 mg/mL |
| 2 | 5 mg/mL | 5.21 mg/mL |
| 3 | 15 mg/mL | 15.62 mg/mL |
| 4 | 80 mg/mL | 83.28 mg/mL |

Procedure for Inhalation Treatment Cohort

Animals were challenged with aerosolized LPS (lipopolysaccharide, 1 mg/mL) for 30 min. Approximately 3 h following end of LPS challenge, animals were administered either vehicle or formulations as described above of acetate salt of cyclo(-OctG-Glu-Thr-Ala-Ser-Ile-Pro-Pro-Gln-Lys-Tyr-$^D$Pro-Pro-) by inhalation (Groups 1-4) over a 30 min period using an eFlow® 30 XL electronic nebulizer (Pari Pharma GmbH, Starnberg, Germany; snout only exposure). All animals were dosed with fMLP (N-formyl-Met-Leu-Phe, 5 mg/kg) approximately 4 h post completion of the LPS challenge via the intratracheal route under transient gaseous anaesthesia at a dose volume of 1 mL/kg. Approximately 2 h after fMLP administration, animals were terminated and a bronchoalveolar lavage (BAL) was performed to evaluate inflammatory cell infiltrate and neutrophil elastase activity. The procedure for the inhalation treatment cohort is summarized in Table 12.

TABLE 12

| Group | Whole body challenge (30 min) | Inhalation treatment; nominal concentration of drug (mg/mL) | Target exposure level (μg/L)* | Treatment dose (mg/kg free base) | Lung dose (mg/kg) (assuming 10% deposition) | Neutrophil elastase activation (1 mL/kg, i.t.) | Animal numbers (PD) |
|---|---|---|---|---|---|---|---|
| 1 | LPS (1 mg/mL) | 0 mg/mL (vehicle) | — | — | — | fMLP (5 mg/kg) | 10 |
| 2 | LPS (1 mg/mL) | 5 mg/mL | 13.4 | 0.3 | 0.03 | fMLP (5 mg/kg) | 10 |
| 3 | LPS (1 mg/mL) | 15 mg/mL | 134 | 3 | 0.3 | fMLP (5 mg/kg) | 10 |
| 4 | LPS (1 mg/mL) | 80 mg/mL | 1340 | 30 | 3 | fMLP (5 mg/kg) | 10 |

*Exposure level (μg/L) based on a 250 g rat.

LPS in 0.9% (w/v) saline fMLP in 1% DMSO in saline

Male rat, Crl:CD (SD), Charles River Laboratories, Wilmington, Massachusetts, USA All animals were terminated for bronchoalveolar lavage approximately 6 h after LPS exposure.

$$\text{Delivered dose } (\mu g/kg) = \frac{C\ (\mu g/L) \times RMV\ (L/\text{min}) \times D\ (\text{min})}{BW\ (\text{kg})}$$

where C = Concentration in air inhaled

RMV = Respiratory minute volume, calculated from the formula: RMV (L/min) = 0.608 × BW $(kg)^{0.852}$ (Ref. 1)

D = Duration of exposure in min

BW = Bodyweight

Ref. 1: D.J. Alexander, C.J. Collins, D.W. Coombs et al., Association of Inhalation Toxicologists (AIT) working party recommendation for standard delivered dose calculation and expression in non-clinical aerosol inhalation toxicology studies with pharmaceuticals; *Inhal. Tox.*, 2008, 20, 1179-1189.

The doses of fMLP and the time points were chosen based upon published data (see e.g. S. Yasui, A. Nagai, K. Aoshiba et al., *Eur. Respir. J.,* 1995, 8, 1293; T. Yang, J. Zhang, K. Sun et al., *Inflamm. Res.* 2012, 61, 563; R. Corteling, D. Wyss, A. Trifilieff, *BMC Pharmacology,* 2002, 2, 1) and experience at Envigo CRS Limited. The dose selection of the drug was based on a previous intratracheal study at Envigo CRS Limited. In this previous study, intratracheal doses of 0.03 to 3 mg/kg of the drug were found to be efficacious in this animal model.

No test item related clinical signs were observed between the dosing period and study termination. Two animals of group 1 (vehicle) died just after fMLP administration due to deep anaesthesia.

Bronchoalveolar Lavage (BAL)

Following confirmation of death, the trachea of an animal was isolated, the tracheal cannula inserted and secured in place, and the airway was lavaged with 3 mL of phosphate buffered saline (PBS). The lavage was repeated twice and in total, three lots of 3 mL of PBS were used. The first lavage aliquot containing cells was placed into a 15 mL centrifuge tube on wet ice (Tube A). The BAL fluid pooled from the second two lavages was placed into a second tube (Tube B). Tube A and B were placed on wet ice until centrifuged. Centrifugation was performed at 800×g for 10 min at ca. 4° C. and the supernantant was harvested. Until neutrophil elastase analysis supernantant was stored at ca. 80° C.

Neutrophil Elastase Activity

Figure 2:
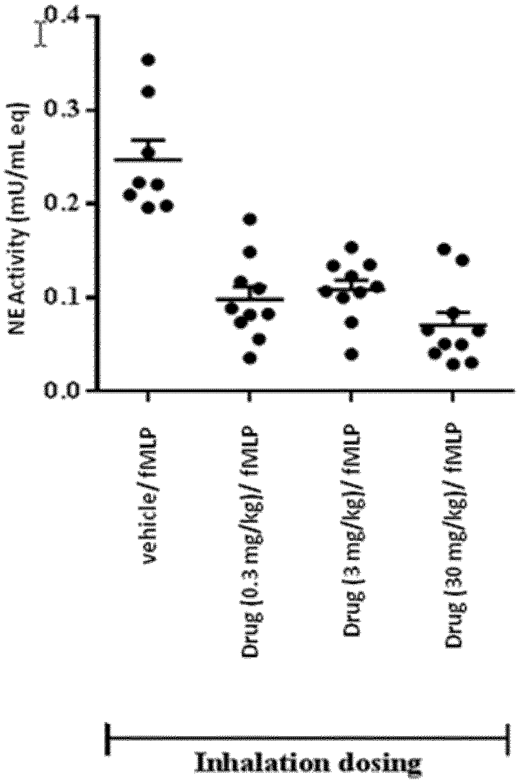

The two aliquots of BAL supernatant were analyzed for neutrophil elastase activity as follows: 120 μL of BAL supernatant from aliquot 1 was transferred to a 96 well plate (Corning #3650). In parallel, a dilution range from 1.6 to 0.025 mU/well of a commercial human neutrophil elastase (hNE, Serva #20927.01) was prepared. 120 μL of each hNE dilution were transferred in duplicate to the 96-well plate. To start the enzymatic reaction, 80 μL of a fluorescent peptide substrate (MeOSuc-Ala-Ala-Pro-Val-AMC) at a final concentration of 500 μM was added to each well and the plate was immediately placed in the victor2v fluorescent reader pre-warmed at 37° C. Fluorescence (Xexc. 485 nm, Xem. 535 nm) was recorded for 2 h at 37° C. Enzyme initial velocity (RFU/min) of all samples was calculated and converted in mU/mL hNE equivalent, using the linear regression equation obtained from the plot (RFU/min vs mU/mL of hNE dilution) of the human neutrophil elastase standard range. The assay was repeated using BAL supernatant from aliquot 2. The neutrophil elastase data reported is a mean of the neutrophil elastase activity from both aliquots. The neutrophil elastase activity in the BAL fluid is presented in Table 13 and FIGS. 1 and 2.

TABLE 13

| Group | Inhalation administation | NE activity (mU/mL eq.) |
|---|---|---|
| 1 | vehicle/fMLP | 0.25 ± 0.02 |
| 2 | drug (0.3 mg/kg)/fMLP | 0.10 ± 0.01**** |
| 3 | drug (3 mg/kg)/fMLP | 0.11 ± 0.01**** |
| 4 | drug (30 mg/kg)/fMLP | 0.07 ± 0.01**** |

Values rounded, precision may not be as displayed.
Data is expressed as mean ± s.e.m.
****$p < 0.0001$ when compared to the vehicle (inhalation)/fMLP treated group.

The drug cyclo(-OctG-Glu-Thr-Ala-Ser-Ile-Pro-Pro-Gln-Lys-Tyr-$^D$Pro-Pro-) administered at doses of 0.3, 3 and 30 mg/kg by inhalation route 3 h post LPS challenge and 1 h prior to fMLP challenge significantly inhibited neutrophil elastase activity in BAL fluid harvested 6 h post LPS challenge.

Phase-Ib Study to Investigate Safety, Tolerability and Pharmacokinetics of Orally Inhaled Single Doses of Acetate Salt of Cyclo(-OctG-Glu-Thr-Ala-Ser-Ile-Pro-Pro-Gln-Lys-Tyr-$^D$Pro-Pro-) in Patients with Cystic Fibrosis In this randomised, double-blind, placebo-controlled, parallel-group (per dose level) dose-escalation study, the safety and tolerability of single ascending doses (SAD) of acetate salt of cyclo(-OctG-Glu-Thr-Ala-Ser-Ile-Pro-Pro-Gln-Lys-Tyr-$^D$Pro-Pro-) administered by inhalation in patients with cystic fibrosis (CF) was investigated. Additionally, the pharmacokinetics of the drug following a single ascending dose in plasma and sputum as well as its pharmacodynamic effect on neutrophil elastase activity in sputum were evaluated.

Treatment

In this study, conducted by Inamed GmbH, Gauting, Germany, 24 subjects with cystic fibrosis, who fulfilled all the inclusion criteria and in whom no exclusion criterion was present, were included and received randomised treatment. They were grouped into 3 dose groups of 8 subjects each. 6 subjects received the formulation described in Example 1 and dilutions thereof and 2 subjects received placebo (0.5% [w/w] aqueous sodium chloride solution adjusted to pH 5.5 with 1 M HCl pharmaceutical grade). The oral inhalation of the above formulation as well as the placebo occurred via the Pari eFlow® XL 30 nebulizer device (Pari Pharma GmbH, Starnberg, Germany). The dose levels and corresponding concentrations of cyclo(-OctG-Glu-Thr-Ala-Ser-Ile-Pro-Pro-Gln-Lys-Tyr-$^D$Pro-Pro-) (active compound) are summarized in Table 14.

TABLE 14

| Dose | Preparation and Volume of nebulizer solution | Concentration |
|---|---|---|
| Dose Level 1 | 80 mg of drug in 4 mL solution | 20 mg/mL |
| Dose Level 2 | 160 mg of drug in 4 mL solution | 40 mg/mL |
| Dose Level 3 | 320 mg of drug in 4 mL solution | 80 mg/mL |

The volume of placebo nebulizer solution corresponded to that of the active compound at a particular dose level. The duration of inhalation was estimated to be between 7 and 20 min. Adverse events were tabulated and summarized according to the current version of Medical Dictionary for Regulatory Activities.

Safety and Tolerability Results

No death, no serious adverse events (AE) and no other significant AE occurred during the study. There were no inhalation-related local AEs. None of the 24 subjects terminated the study early because of AE.

In total, 6 AEs, all of them treatment-emergent adverse events (TEAEs), were recorded in 6 subjects. The most frequently reported terms were 'dizziness' and 'headache' with 2 events each. All 6 TEAEs were regarded as being not related to the active compound. None of the TEAEs was rated as severe. AE duration was transient. All 6 AEs resolved without sequels. Regarding the number of AEs as well as their intensity and causal relationship to the study medication, no obvious difference between the dose levels became apparent. Throughout the study, the majority of clinical laboratory values as well as ECG and vital signs results remained within the respective reference ranges. Any deviating findings were clinically not relevant and well in line with the extent of deviations usually observed in studies with CF patients. The majority of results from lung function tests were as expected of patients with CF.

Pharmacokinetic Assessments

The following pharmacokinetic parameters were assessed for cyclo(-OctG-Glu-Thr-Ala-Ser-Ile-Pro-Pro-Gln-Lys-Tyr-$^{D}$Pro-Pro-) (active compound):

Plasma:

$AUC_{0-\infty}$, $AUC_{0-\infty}/D$, $C_{max}$, $C_{max}/D$ of active compound in plasma as primary variables and $t_{max}$, $t_{1/2}$, $\lambda_2$, $AU_{0-tlast}$ of active compound in plasma as secondary variables.

Sputum:

Concentrations of active compound in sputum were calculated and $C_{max}$ and $AUC_{0-tlast}$ were determined.

Sampling and Sample Processing for Plasma Samples

Blood samples for the determination of the plasma concentrations of active compound were taken at the following points in time:

On Day 1 at pre-dose, 10 min, and 0.5 h, 1 h, 2 h, 3 h, 4 h, 6 h, 8 h, 12 h, 15 h, and on Day 2 at 24 h post dose (after start of inhalation).

The samples were collected in closed K3-EDTA plasma sampling tubes (Monovette® Sarstedt, Germany). The accepted time-interval for sample handling procedures for each individual study sample, i.e., the time between sample collection and sample centrifugation had not to exceed 60 min, and the time between the end of centrifugation and sample freezing had also not to exceed 60 min.

The samples were centrifuged at approximately 4° C. (±2° C.) at 2200×g for 15 min.

The resulting plasma supernatant was then transferred into 2 polypropylene tubes ($1^{st}$ aliquot of at least 1 mL and backup) and frozen in upright position below 20° C.

Samples were stored in a freezer under continuous temperature control below 20° C. from the day after sample collection until shipment (dry ice with a thermo-logging device) to the bioanalytical site (Pharmacelsus GmbH, Saarbrücken, Germany).

Sampling and Sample Processing for Sputum Samples

Spontaneous sputum samples for PK assessments were collected during the following time intervals/periods:

On Day −1 as soon as possible after the subject's arrival at the study site (blank PK), on Day 1 in the period of time between 1 h and 3 h after start of inhalation, and in the morning of Day 2, at approx. 24 h after start of inhalation. Moreover, any spontaneous sputum expectoration between 0-1 h after start of inhalation was collected.

Spontaneous sputum samples were collected in polystyrene Petri dishes and put on ice immediately. All processing steps had to be performed with cold reagents and on ice whenever possible. Plugs were separated from saliva, but the latter was not discarded. If a sputum sample was taken for both PK and neutrophil elastase activity in sputum analysis, the plug was split in 2 approximately equal parts. One part was processed for PK analysis the other one for evaluation of neutrophil elastase activity in sputum.

For PK processing, the resulting plug was split in approximately 2 equal parts. These were transferred into 2 transfer tubes for PK evaluation (SP1) and PK Backup (SP3). Up to 1.0 mL saliva was transferred into another transfer tube for PK evaluation (SP2). The remaining saliva in the Petri dish was discarded. The weight of the sputum samples (SP1+SP3) was determined and all samples were immediately put on dry ice for freezing. After freezing, samples were stored in an upright position at −80±10° C. The sputum and saliva samples for PK evaluation (SP1+SP2) were shipped to Pharmacelsus GmbH on dry ice. The backup sputum samples (SP3) were stored at −80±10° C. at Inamed GmbH, Gauting, Germany.

Bioanalytical Methods

For the analysis of active compound in plasma, a validated and highly sensitive liquid chromatography tandem mass spectrometry (LC-MS/MS) method was used.

For the analysis of active compound in sputum a validated or, where not available, 'fit-for-purpose' highly sensitive liquid chromatography tandem mass spectrometry (LC-MS/MS) method was to be used.

The bioanalytical procedures were performed according to current Good Laboratory Practice (GLP) regulations, US Food and Drug Administration (FDA) and EMA validation requirements for bioanalytical assays and were outlined in applicable SOPs including regulations for routine analysis and general regulations for analysis.

Derived Pharmacokinetic Parameters

The pharmacokinetic parameters mentioned above were calculated based on actual blood and sputum sampling times using non-compartmental procedures.

Plasma Concentration-Time Curves and Derived Pharmacokinetic Parameters of Cyclo(-OctG-Glu-Thr-Ala-Ser-Ile-Pro-Pro-Gln-Lys-Tyr-$^{D}$Pro-Pro-)

Figure 3:
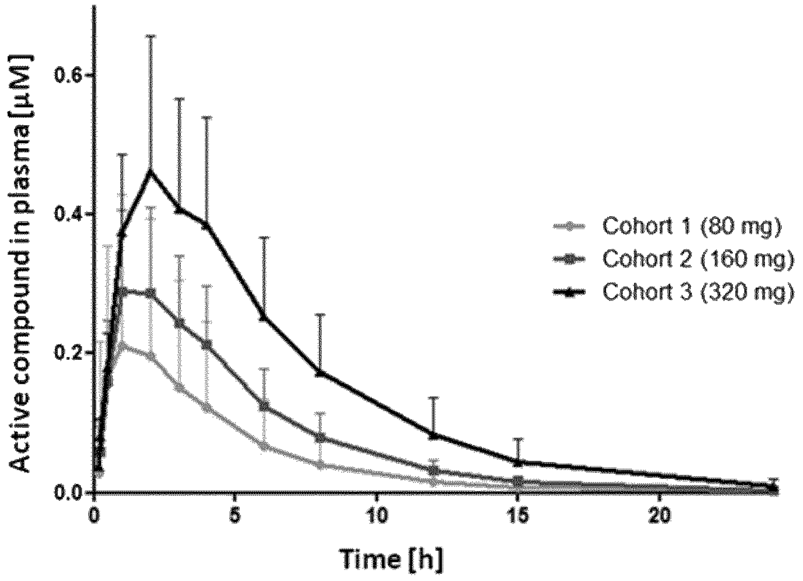
FIG. 3 shows the mean plasma concentration-time curves of single ascending doses (80 mg, 160 mg and 320 mg per cohort) of cyclo(-OctG-Glu-Thr-Ala-Ser-Ile-Pro-Pro-Gln-Lys-Tyr-$^{D}$Pro-Pro-) administered by inhalation to patients with cystic fibrosis. These curves show typical profiles similar to profiles of curves resulting from comparable doses of active compound inhaled by healthy subjects.

The mean plasma concentration-time curves of active compound are shown in FIG. 3.

The curves of active compound show typical profiles and similar to the results of healthy subjects inhaling comparable doses of active compound, its first plasma concentrations were detected early on in patients with CF.

Plasma concentrations of active compound increased to reach their respective peaks ($t_{max}$, mean) at 1.3 h in dose group 1, at 1.5 h in dose group 2 and at 2.3 h in dose group 3. Thereafter, plasma concentrations of active compound declined with a mean terminal half-life of 4.1 h in dose group 1, 3.5 h in dose group 2 and 3.8 h in dose group 3. 24 hours after inhalation, active compound could still be detected in subjects of all dose groups, with mean plasma concentrations of 2.8 ng/mL in dose group 1, 4.4 ng/mL in dose group 2 and 15.2 ng/mL in dose group 3.

Sputum Concentration of Cyclo(-OctG-Glu-Thr-Ala-Ser-Ile-Pro-Pro-Gln-Lys-Tyr-$^{D}$Pro-Pro-)

Figure 4:
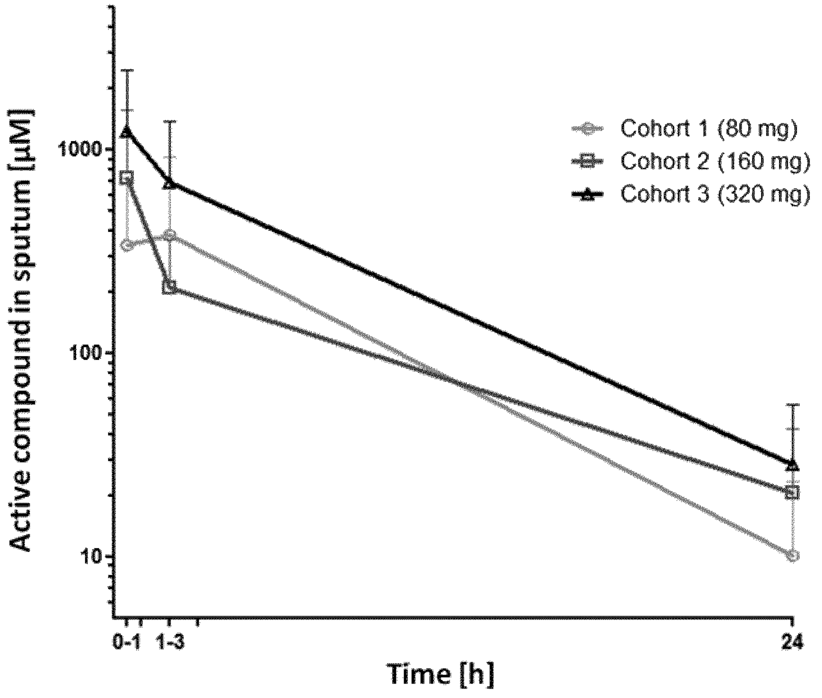
FIG. 4 shows the mean sputum concentrations of cyclo(-OctG-Glu-Thr-Ala-Ser-Ile-Pro-Pro-Gln-Lys-Tyr-$^{D}$Pro-Pro-) administered by inhalation to patients with cystic fibrosis as single ascending doses (80 mg, 160 mg and 320 mg per cohort). Data are displayed versus time. Comparison of concentrations of active compound in sputum (FIG. 4) and plasma (FIG. 3) shows that concentrations of active compound in sputum are approximately $10^3$ fold higher than in plasma.

The mean sputum concentrations of active compound are shown in FIG. 4.

Already at the first sputum sampling time point after inhalation (0-1 h sampling interval), active compound was detected in the majority of subjects across all dose groups. The concentration of active compound in sputum increased by dose, with the highest mean (SD) concentration values of 0.6 (0.79) g/L (dose group 1, 1-3 h sampling interval), 1.1 (1.23) g/L (dose group 2, 0-1 h sampling interval) and 1.8 (1.81) g/L (dose group 3, 0-1 h sampling interval). Active compound could be still detected in sputum across subjects of all dose groups at 24 h after inhalation.

Pharmacodynamic Assessments

The pharmacodynamic effect of ascending single doses of active compound was investigated by evaluation of neutrophil elastase (NE) activity in sputum using FRET (fluorescence resonance energy transfer) assay after PBS aliquotation and freezing.

Sampling and Sample Processing for Sputum Samples

Spontaneous sputum samples for evaluation of neutrophil elastase (NE) activity were collected during the following time intervals/periods:

On the day of screening, if possible, for baseline assessment of NE activity, on Day −1 as soon as possible after the subject's arrival at the study site for baseline assessment of NE activity, on Day 1 in the period of time between 1 h and 3 h after start of inhalation, and in the morning of Day 2, at approx. 24 h after start of inhalation.

Spontaneous sputum samples were collected in polystyrene Petri dishes and put on ice immediately. All processing steps had to be performed with cold reagents and on ice whenever possible. Plugs were separated from saliva, but the latter was not discarded. If a sputum sample was taken for both PK and NE activity in sputum analysis, the plug was split in 2 approximately equal parts. One part was processed for evaluation of NE activity in sputum the other one for PK analysis, as described above.

For evaluation of NE activity in sputum, at first, the weight of the sputum sample was determined and 8 mL cold phosphate-buffered saline (PBS) per gram purified sputum was added. The sample was vortexed for 30 s at room temperature (15-24° C.). Then, the soluble fraction was separated from the sputum pellet by centrifugation (10 min at 1000×g and 4° C.). The supernatant was transferred to a fresh tube.

Remaining insoluble particles were separated by a second centrifugation step at 3500×g for 15 min at 4° C. If the supernatant was not aliquoted immediately, the PBS/sputum supernatant was transferred to a fresh tube.

10 aliquots of 50 μL PBS/sputum were transferred into transfer tubes for evaluation. Moreover, 4 aliquots of 50 μL PBS/sputum were transferred into transfer tubes as backup. In case there was a leftover, the remaining volume was immediately transferred into a transfer tube for evaluation. Any leftover exceeding 2.0 mL was discarded.

Samples were frozen immediately and stored in an upright position at −80±10° C.

PBS/Sputum samples were shipped to MLM Medical Labs GmbH, Mönchengladbach, Germany, on dry ice. PBS/Sputum backup samples were stored at −80±10° C. at Inamed GmbH, Gauting, Germany.

Bioanalytical Methods

The NE activity in sputum was evaluated by using a FRET elastase assay adapted from an assay described in *Nature Protocols,* 2008, 3, 991 (B. Korkmaz, S. Attucci, M. A. Juliano et al.) and validated by MLM Medical Labs GmbH, Mönchengladbach, Germany.

The assay is based on the reaction of human neutrophil elastase with the substrate 2Abz-Ala-Pro-Glu-Glu-Ile-Met-Arg-Arg-Gln-Tyr($3NO_2$)—OH (GeneCust Europe S. A., Ellange, Luxembourg, #P160301-SY452824). By adding the substrate solution the enzyme reaction is started and the elastase present in the samples reacts with added substrate. The product of the reaction is detected through fluorescence measurement and the initial reaction velocity is determined. The concentration of active elastase in the unknown samples is back-calculated using the calibration curve calculated from the standards.

An elastase reference stock solution (human neutrophil elastase [ELA2], Höltzel Diagnostika, Köln, Germany, #PN31255) with known enzymatic activity was prepared. The exact active elastase enzyme concentration was determined by titration against an alpha 1-antitrypsin solution (Athens Research and Technology, Athens, USA, #16-16-011609), with a defined concentration. The active elastase reference stock solution was adjusted by addition of PBS to a concentration of 3000 nM and aliquots were stored at −80° C.

The FRET assay was performed in 96 well white microtiter plates in total volume of 100 μL per well. PBS sputum dilutions of 1:5, 1:50 and 1:100 in elastase reaction buffer (50 mM HEPES, pH 7.4, 750 mM NaCl, 0.05% [v/v] NP-40) were prepared, 5 uL loaded per well and 90 uL elastase reaction buffer were added. A 5 mM substrate stock solution of 2Abz-Ala-Pro-Glu-Glu-Ile-Met-Arg-Arg-Gln-Tyr($3NO_2$)—OH in 30% (v/v) N,N-dimethylformamide/water was prepared and further diluted to 400 nM by addition of elastase reaction buffer. 5 uL of the 400 nM substrate solution were added to the wells and the reaction velocity $V_i$ was determined by FRET at Exc:320 nm-Emiss: 420 nm. The concentration of active elastase in PBS sputum was determined by comparison of reaction velocities of defined dilutions from the active elastase reference stock solution.

The analytical measuring range of this method was 115.00-2880.00 ng/mL. Intra- and inter-assay coefficients of variation were ≤17.14% and ≤8.96%, respectively.

Active Neutrophil Elastase in Sputum

Figure 5:
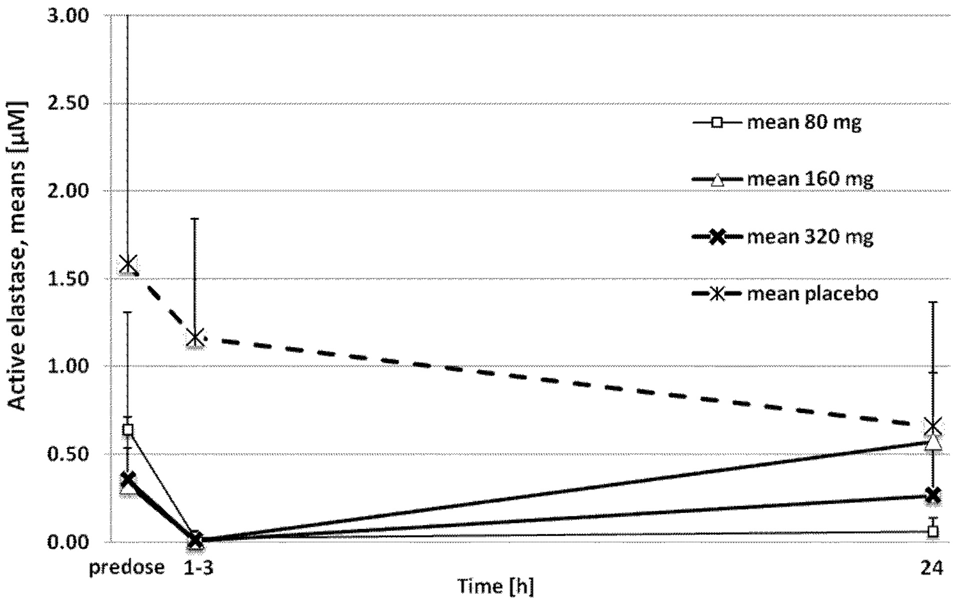
FIG. 5 shows the effects on active neutrophil elastase in sputum of patients with cystic fibrosis induced by cyclo(-OctG-Glu-Thr-Ala-Ser-Ile-Pro-Pro-Gln-Lys-Tyr-$^{D}$Pro-Pro-) administered by inhalation to patients with cystic fibrosis as single ascending doses (80 mg, 160 mg and 320 mg per cohort). The data are displayed versus time and depicted as means. Additionally, data of placebo are depicted as well.

Mean concentrations of active NE are shown in FIG. 5.

Active NE concentration results were highly variable throughout. When measured by FRET assay, mean (SD) concentrations of active NE in sputum on Day −1 (predose) were 18823.6 (19758.72) ng/mL for dose level 1, 9548.7 (6222.55) ng/mL for dose level 2 and 10480.7 (10528.00) ng/mL for dose level 3. The mean (SD) active NE concentration for placebo subjects at pre-dose was 46711.8 (48456.86) ng/mL.

The concentration of active NE in sputum strongly decreased in subjects after inhaling active compound. Mean (SD) concentration values at 1-3 h after inhalation were 612.5 (1218.62) ng/mL for dose level 1 and 115.0 (0.00) ng/mL for dose levels 2 and 3. The mean (SD) value for subjects inhaling placebo at 1-3 h after inhalation was 34370.0 (19988.11) ng/mL.

Mean (SD) active NE concentrations in sputum at 24 h after inhalation were 1467.7 (2154.43) ng/mL for dose level 1, 16849.4 (23518.56) ng/mL for dose level 2 and 7712.5 (11394.04) ng/mL for dose level 3. The mean (SD) active NE concentration at 24 h for placebo subjects was 19338.8 (9062.32) ng/mL.

PHARMACODYNAMIC CONCLUSIONS

The mean concentration of active NE in the sputum of patients with CF strongly decreased after single-dose inhalation of active compound administered by a formulation described in Example 1. In the dose range examined, the extent of this response appeared to be independent of the dose administered. Although difficult to judge due to high data variability, the mean concentration of active NE in sputum apparently returned to baseline levels at 24 h after inhalation of active compound. The inhalation of placebo solution had no distinct effect on the mean concentration of active NE in sputum. These clinical results show that cyclo(-OctG-Glu-Thr-Ala-Ser-Ile-Pro-Pro-Gln-Lys-Tyr-$^{D}$Pro-Pro-) administered by a formulation described in Example 1 inhibits NE in the sputum of patients with CF.

The invention claimed is:

1. A pharmaceutical aerosol for pulmonary administration comprising a dispersed liquid phase and a continuous gas phase, wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-);

or pharmaceutically acceptable salt thereof; wherein

OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7;

the aerosol being prepared from a liquid pharmaceutical composition comprising the active compound cyclo(-OctG-Glu-Thr-Ala-Ser-Ile-Pro-Pro-Gln-Lys-Tyr-$^{D}$Pro-Pro-); or pharmaceutically acceptable salt thereof; in a concentration within a range from about 4 mg/mL to about 100 mg/mL, having a dynamic viscosity in the range from about 0.8 mPas to about 1.7 mPas and a surface tension in the range from about 25 mN/m to 80 mN/m.

2. The pharmaceutical aerosol according to claim 1, wherein the counter ion of the active compound is acetate.

3. The pharmaceutical aerosol according to claim 1 being emitted from an aerosol generator at a rate of at least about 0.1 mL dispersed liquid phase per minute.

4. The pharmaceutical aerosol according to claim 1 being emitted from an aerosol generator at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-); or pharmaceutically acceptable salt thereof; per minute.

5. A liquid pharmaceutical composition for preparing the pharmaceutical aerosol according to claim 1 comprising the active compound cyclo(-OctG-Glu-Thr-Ala-Ser-Ile-Pro-Pro-Gln-Lys-Tyr-$^{D}$Pro-Pro-); or pharmaceutically acceptable salt thereof; in a concentration within a range from about 4 mg/mL to about 100 mg/mL and sodium chloride.

6. The liquid pharmaceutical composition according to claim 5 comprising at least one taste-modifying excipient.

7. A solid pharmaceutical composition for preparing the liquid pharmaceutical composition of claim 5, wherein the solid pharmaceutical composition comprises the active compound cyclo(-OctG-Glu-Thr-Ala-Ser-Ile-Pro-Pro-Gln-Lys-Tyr-$^{D}$Pro-Pro-); or pharmaceutically acceptable salt thereof; and wherein the solid composition is dissolvable or dispersible in an aqueous liquid solvent, and wherein the liquid composition comprises a concentration within a range from about 4 mg/mL to about 100 mg/mL of the active compound; or pharmaceutically acceptable salt thereof.

8. The solid pharmaceutical composition according to claim 7, wherein pharmaceutically acceptable salt of the active compound is an acetate.

9. A kit for the preparation and delivery of a pharmaceutical aerosol for pulmonary administration comprising a dispersed liquid phase and a continuous gas phase;

wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-); or pharmaceutically acceptable salt thereof; wherein OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7;

and wherein the kit comprises a nebulizer and a liquid composition comprising a concentration within a range from about 4 mg/mL to about 100 mg/mL of the active compound; or pharmaceutically acceptable salt thereof, having a dynamic viscosity in the range from about 0.8 mPas to about 1.7 mPas and a surface tension in the range from about 25 mN/m to 80 mN/m; or wherein the dispersed liquid phase (a) comprises aqueous droplets comprising the active compound cyclo(-OctG-Glu-Thr-Ala-Ser-Ile-Pro-Pro-Gln-Lys-Tyr-$^{D}$Pro-Pro-); or pharmaceutically acceptable salt thereof; wherein OctG is (S)-2-aminodecanoic acid;

$^{D}$Pro is D-proline;

(b) has a mass median diameter from about 1.5 μm to about 5 μm; and (c) has a droplet size distribution having a geometrical standard deviation from about 1.2 to about 1.7; and wherein the kit comprises a nebulizer and a solid pharmaceutical composition for preparing the liquid composition, wherein the solid composition comprises the active compound cyclo(-OctG-Glu-Thr-Ala-Ser-Ile-Pro-Pro-Gln-Lys-Tyr-$^{D}$Pro-Pro-); or pharmaceutically acceptable salt thereof; and wherein the solid composition is dissolvable or dispersible in an aqueous liquid solvent, and wherein the liquid composition comprises a concentration within a range from about 4 mg/mL to about 100 mg/mL of the active compound; or pharmaceutically acceptable salt thereof, having a dynamic viscosity in the range from about 0.8 mPas to about 1.7 mPas and a surface tension in the range from about 25 mN/m to 80 mN/m.

10. The kit according to claim 9, wherein the counter ion pharmaceutically acceptable salt of the active compound is an acetate.

11. The kit according to claim 9, wherein the nebulizer is selected from the group consisting of jet nebulizers, ultrasonic nebulizers, piezoelectronic nebulizers, jet collision nebulizers, electrohydrodynamic nebulizers, capillary force nebulizers, perforated membrane nebulizers and perforated vibrating membrane nebulizers.

12. The kit according to claim 9, wherein the nebulizer is adapted to be capable of aerosolizing the liquid composition at a rate of at least about 0.8 mg of the active compound cyclo(-OctG-Glu-Thr-Ala-Ser-Ile-Pro-Pro-Gln-Lys-Tyr-$^{D}$Pro-Pro-); or pharmaceutically acceptable salt thereof; per minute.

13. The kit according to claim 9, wherein at least about 70 wt.-% of a loaded dose of the active compound cyclo(-OctG-Glu-Thr-Ala-Ser-Ile-Pro-Pro-Gln-Lys-Tyr-$^{D}$Pro-Pro-); or pharmaceutically acceptable salt thereof; is comprised of droplets having a mass median diameter of not more than about 5 μm.

14. A method of preparing and delivering an aerosol for pulmonary administration, said method comprising the steps of (a) providing a liquid pharmaceutical composition comprising the active compound cyclo(-OctG-Glu-Thr-Ala-Ser-Ile-Pro-Pro-Gln-Lys-Tyr-$^{D}$Pro-Pro-); or pharmaceutically acceptable salt thereof; in a concentration within a range from about 4 mg/mL to about 100 mg/mL;

or providing a solid pharmaceutical composition for preparing the liquid composition, wherein the composition comprises the active compound cyclo(-OctG-Glu-Thr-Ala-Ser-Ile-Pro-Pro-Gln-Lys-Tyr-$^{D}$Pro-Pro-); or pharmaceutically acceptable salt thereof; and wherein the solid composition is dissolvable or dispersible in an aqueous liquid solvent, and wherein the liquid composition comprises a concentration within a range from about 4 mg/mL to about 100 mg/mL of the active compound; or pharmaceutically acceptable salt thereof, having a dynamic viscosity in the range from about 0.8 mPas to about 1.7 mPas and a surface tension in the range from about 25 mN/m to 80 mN/m;

(b) providing a nebulizer capable of aerosolizing said liquid pharmaceutical composition at a mean delivery rate of at least about 0.8 mg of the active compound cyclo(-OctG-Glu-Thr-Ala-Ser-Ile-Pro-Pro-Gln-Lys-Tyr-$^{D}$Pro-Pro-); or pharmaceutically acceptable salt thereof; per minute; the nebulizer being further adapted to emit an aerosol comprising a dispersed liquid phase having a mass median diameter from about 1.5 μm to about 5 μm; and having a droplet size distribution having a geometrical standard deviation from about 1.2 to about 1.7; and (c) operating the nebulizer to aerosolize the liquid pharmaceutical composition.

* * * * *